(12) United States Patent
Huebner

(10) Patent No.: US 7,326,212 B2
(45) Date of Patent: Feb. 5, 2008

(54) BONE PLATES WITH REFERENCE MARKS

(75) Inventor: Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 714 days.

(21) Appl. No.: 10/717,399

(22) Filed: Nov. 19, 2003

(65) Prior Publication Data
US 2004/0102776 A1 May 27, 2004

Related U.S. Application Data

(60) Provisional application No. 60/427,908, filed on Nov. 19, 2002, provisional application No. 60/512,136, filed on Oct. 17, 2003.

(51) Int. Cl.
*A61B 17/56* (2006.01)
*A61F 2/30* (2006.01)

(52) U.S. Cl. .................................................. 606/69
(58) Field of Classification Search ............... 606/69, 606/70, 71, 72, 73, 54, 58, 59
See application file for complete search history.

(56) References Cited

U.S. PATENT DOCUMENTS

| 820,503 | A | 5/1906 | Krengel et al. |
|---|---|---|---|
| 869,697 | A | 10/1907 | Eilhauer et al. |
| 1,105,105 | A | 7/1914 | Sherman |
| 1,345,425 | A | 7/1920 | Wells |
| 1,789,060 | A | 1/1931 | Weisenbach |
| 1,889,239 | A | 11/1932 | Crowley |
| 2,406,832 | A | 9/1946 | Hardinge |
| 2,443,363 | A | 6/1948 | Townsend et al. |
| 2,489,870 | A | 11/1949 | Dzus |
| 2,494,229 | A | 1/1950 | Collison |
| 2,500,370 | A | 3/1950 | McKibbin |
| 2,526,959 | A | 10/1950 | Lorenzo |
| 2,580,821 | A | 1/1952 | Nicola |
| 2,583,896 | A | 1/1952 | Siebrandt |
| 2,737,835 | A | 3/1956 | Herz |
| 3,025,853 | A | 3/1962 | Mason |
| 3,072,423 | A | 1/1963 | Charlton |
| 3,171,518 | A | 3/1965 | Bergmann |
| 3,244,170 | A | 4/1966 | McElvenny |
| 3,346,894 | A | 10/1967 | Lemelson |
| 3,386,437 | A | 6/1968 | Treace |
| 3,488,779 | A | 1/1970 | Christensen |
| 3,489,143 | A | 1/1970 | Halloran |
| 3,593,709 | A | 7/1971 | Halloran |
| 3,604,414 | A | 9/1971 | Borges |

(Continued)

FOREIGN PATENT DOCUMENTS

AU     89750/91     2/1992

(Continued)

OTHER PUBLICATIONS

English Abstract for EP 773004 A1.*

(Continued)

*Primary Examiner*—Anuradha Ramana
(74) *Attorney, Agent, or Firm*—Kolisch Hartwell, P.C.

(57) ABSTRACT

Bone plates having reference marks, and methods of using the bone plates to fix bones.

21 Claims, 6 Drawing Sheets

U.S. PATENT DOCUMENTS

| | | |
|---|---|---|
| 3,716,050 A | 2/1973 | Johnston |
| 3,741,205 A | 6/1973 | Markolf et al. |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,119,092 A | 10/1978 | Gil |
| 4,187,840 A | 2/1980 | Watanabe |
| 4,187,841 A | 2/1980 | Knutson |
| 4,201,215 A | 5/1980 | Crossett et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,484,570 A | 11/1984 | Sutter et al. |
| 4,493,317 A | 1/1985 | Klaue |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,919,119 A * | 4/1990 | Jonsson et al. ............ 606/54 |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,988,350 A | 1/1991 | Herzberg |
| 5,002,544 A | 3/1991 | Klaue et al. |
| 5,006,120 A | 4/1991 | Carter |
| 5,013,315 A | 5/1991 | Barrows |
| 5,015,248 A | 5/1991 | Burstein et al. |
| 5,021,056 A | 6/1991 | Hofmann et al. |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,129,899 A | 7/1992 | Small et al. |
| 5,133,718 A | 7/1992 | Mao |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,737 A | 4/1993 | Leibinger et al. |
| 5,207,676 A * | 5/1993 | Canadell et al. ............ 606/54 |
| 5,234,431 A | 8/1993 | Keller |
| 5,254,119 A | 10/1993 | Schreiber |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,364,398 A | 11/1994 | Chapman et al. |
| 5,364,399 A | 11/1994 | Lowery et al. |
| 5,376,091 A * | 12/1994 | Hotchkiss et al. ........... 606/55 |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Proctor et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,607,426 A | 3/1997 | Ralph et al. |
| 5,643,261 A | 7/1997 | Schafer et al. |
| 5,643,265 A | 7/1997 | Errico et al. |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |

| | | | | | | |
|---|---|---|---|---|---|---|
| 5,904,683 | A | 5/1999 | Pohndorf et al. | 6,454,769 B2 | 9/2002 | Wagner et al. |
| 5,916,216 | A | 6/1999 | DeSatnick et al. | 6,454,770 B1 | 9/2002 | Klaue |
| 5,919,195 | A | 7/1999 | Wilson et al. | 6,458,133 B1 | 10/2002 | Lin |
| 5,928,234 | A | 7/1999 | Manspeizer | 6,503,250 B2 | 1/2003 | Paul |
| 5,931,839 | A | 8/1999 | Medoff | 6,508,819 B1 | 1/2003 | Orbay |
| 5,938,664 | A | 8/1999 | Winquist et al. | 6,514,274 B1 | 2/2003 | Boucher et al. |
| 5,941,878 | A | 8/1999 | Medoff | 6,520,965 B2 | 2/2003 | Chervitz et al. |
| 5,951,557 | A | 9/1999 | Luter | 6,527,775 B1 | 3/2003 | Warburton |
| 5,954,722 | A | 9/1999 | Bono | 6,533,789 B1 | 3/2003 | Hall, IV et al. |
| 5,964,763 | A | 10/1999 | Incavo et al. | 6,547,790 B2 | 4/2003 | Harkey et al. |
| 5,968,046 | A | 10/1999 | Castleman | 6,565,570 B2 | 5/2003 | Sterett et al. |
| 5,968,047 | A | 10/1999 | Reed | 6,592,578 B2 | 7/2003 | Henniges et al. |
| 5,973,223 | A | 10/1999 | Tellman et al. | 6,595,993 B2 | 7/2003 | Donno et al. |
| 6,001,099 | A | 12/1999 | Huebner | 6,602,255 B1 | 8/2003 | Campbell et al. |
| 6,004,323 | A | 12/1999 | Park et al. | 6,623,486 B1 | 9/2003 | Weaver et al. |
| 6,004,353 | A | 12/1999 | Masini | 6,623,487 B1 | 9/2003 | Goshert |
| 6,007,535 | A | 12/1999 | Rayhack et al. | 6,682,531 B2 | 1/2004 | Winquist et al. |
| 6,022,350 | A | 2/2000 | Ganem | 6,682,533 B1 | 1/2004 | Dinsdale et al. |
| 6,027,504 | A | 2/2000 | McGuire | 6,689,139 B2 | 2/2004 | Horn |
| 6,053,915 | A | 4/2000 | Bruchmann | 6,695,846 B2 | 2/2004 | Richelsoph et al. |
| 6,077,266 | A | 6/2000 | Medoff | 6,706,046 B2 | 3/2004 | Orbay et al. |
| 6,077,271 | A | 6/2000 | Huebner et al. | 6,712,820 B2 | 3/2004 | Orbay |
| 6,093,188 | A | 7/2000 | Murray | 6,719,759 B2 | 4/2004 | Wagner et al. |
| 6,096,040 | A | 8/2000 | Esser | 6,730,090 B2 | 5/2004 | Orbay et al. |
| 6,113,603 | A | 9/2000 | Medoff | 6,730,091 B1 | 5/2004 | Pfefferle et al. |
| 6,117,160 | A | 9/2000 | Bonutti | 6,736,819 B2 | 5/2004 | Tipirneni |
| 6,123,709 | A | 9/2000 | Jones | 6,767,351 B2 | 7/2004 | Orbay et al. |
| 6,129,728 | A | 10/2000 | Schumacher et al. | 6,793,658 B2 | 9/2004 | LeHuec et al. |
| 6,129,730 | A | 10/2000 | Bono et al. | 6,821,278 B2 | 11/2004 | Frigg et al. |
| 6,139,548 | A | 10/2000 | Errico | 6,858,031 B2 | 2/2005 | Morrison et al. |
| 6,152,927 | A | 11/2000 | Farris et al. | 6,866,665 B2 | 3/2005 | Orbay |
| 6,159,213 | A | 12/2000 | Rogozinski | 6,893,444 B2 | 5/2005 | Orbay |
| 6,179,839 | B1 | 1/2001 | Weiss et al. | 6,955,677 B2 | 10/2005 | Dahners |
| 6,183,475 | B1 | 2/2001 | Lester et al. | 2001/0011172 A1 | 8/2001 | Orbay et al. |
| 6,193,721 | B1 | 2/2001 | Michelson | 2002/0004660 A1 | 1/2002 | Henniges et al. |
| 6,197,028 | B1 | 3/2001 | Ray et al. | 2002/0032446 A1 | 3/2002 | Orbay |
| 6,221,073 | B1 | 4/2001 | Weiss et al. | 2002/0055741 A1 | 5/2002 | Schlapfer et al. |
| 6,224,602 | B1 | 5/2001 | Hayes | 2002/0128654 A1 | 9/2002 | Steger et al. |
| 6,228,087 | B1 | 5/2001 | Fenaroli et al. | 2002/0143336 A1 | 10/2002 | Hearn |
| 6,235,033 | B1 | 5/2001 | Brace et al. | 2002/0143338 A1 | 10/2002 | Orbay et al. |
| 6,235,034 | B1 | 5/2001 | Bray | 2002/0147453 A1 | 10/2002 | Gambale |
| 6,238,396 | B1 | 5/2001 | Lombardo | 2002/0151899 A1 | 10/2002 | Bailey et al. |
| 6,258,092 | B1 | 7/2001 | Dall | 2002/0156474 A1 | 10/2002 | Wack et al. |
| 6,261,291 | B1 | 7/2001 | Talaber et al. | 2002/0183752 A1 | 12/2002 | Steiner et al. |
| 6,273,889 | B1 | 8/2001 | Richelsoph | 2003/0040748 A1 | 2/2003 | Aikins et al. |
| 6,283,969 | B1 | 9/2001 | Grusin et al. | 2003/0055429 A1 | 3/2003 | Ip et al. |
| 6,290,703 | B1 | 9/2001 | Ganem | 2003/0105461 A1 | 6/2003 | Putnam |
| 6,302,883 | B1 | 10/2001 | Bono | 2003/0149434 A1 | 8/2003 | Paul |
| 6,302,884 | B1 | 10/2001 | Wellisz et al. | 2003/0153918 A1 | 8/2003 | Putnam et al. |
| 6,302,887 | B1 | 10/2001 | Spranza et al. | 2003/0233093 A1 | 12/2003 | Moles et al. |
| 6,306,136 | B1 | 10/2001 | Baccelli | 2004/0102775 A1 | 5/2004 | Huebner |
| 6,312,431 | B1 | 11/2001 | Asfora | 2004/0102777 A1 | 5/2004 | Huebner |
| 6,315,779 | B1 | 11/2001 | Morrison et al. | 2004/0102778 A1 | 5/2004 | Huebner et al. |
| 6,322,562 | B1 | 11/2001 | Wolter | 2004/0116930 A1 | 6/2004 | O'Driscoll et al. |
| 6,325,803 | B1 | 12/2001 | Schumacher et al. | 2004/0127901 A1 | 7/2004 | Huebner et al. |
| 6,331,179 | B1 | 12/2001 | Freid et al. | 2004/0127903 A1 | 7/2004 | Schlapfer et al. |
| 6,336,927 | B2 | 1/2002 | Rogozinski | 2004/0153073 A1 | 8/2004 | Orbay |
| 6,338,734 | B1 | 1/2002 | Burke et al. | 2004/0193164 A1 | 9/2004 | Orbay |
| 6,342,055 | B1 | 1/2002 | Eisermann et al. | 2004/0193165 A1 | 9/2004 | Orbay |
| 6,342,075 | B1 | 1/2002 | MacArthur | 2004/0220566 A1 | 11/2004 | Bray |
| 6,355,036 | B1 | 3/2002 | Nakajima | 2004/0260291 A1 | 12/2004 | Jensen |
| 6,355,042 | B2 | 3/2002 | Winquist | 2004/0260292 A1 | 12/2004 | Orbay et al. |
| 6,358,250 | B1 | 3/2002 | Orbay | 2004/0260293 A1 | 12/2004 | Orbay et al. |
| 6,364,881 | B1 | 4/2002 | Apgar et al. | 2004/0260294 A1 | 12/2004 | Orbay et al. |
| 6,364,882 | B1 | 4/2002 | Orbay | 2004/0260295 A1 | 12/2004 | Orbay et al. |
| 6,364,883 | B1 | 4/2002 | Santilli | 2005/0015089 A1 | 1/2005 | Young et al. |
| 6,379,354 | B1 | 4/2002 | Rogozinski | 2005/0049593 A1 | 3/2005 | Duong et al. |
| 6,379,364 | B1 | 4/2002 | Brace et al. | 2005/0065520 A1 | 3/2005 | Orbay |
| 6,402,756 | B1 | 6/2002 | Ralph et al. | 2005/0065522 A1 | 3/2005 | Orbay |
| 6,413,259 | B1 | 7/2002 | Lyons et al. | 2005/0065523 A1 | 3/2005 | Orbay |
| 6,428,542 | B1 | 8/2002 | Michelson | 2005/0065524 A1 | 3/2005 | Orbay |
| 6,436,103 | B1 | 8/2002 | Suddaby | 2005/0065528 A1 | 3/2005 | Orbay |
| 6,440,135 | B2 | 8/2002 | Orbay et al. | 2005/0085818 A1 | 4/2005 | Huebner |

| | | | |
|---|---|---|---|
| 2005/0085819 A1 | 4/2005 | Ellis et al. | |
| 2005/0131413 A1 | 6/2005 | O'Driscoll et al. | |
| 2005/0159747 A1 | 7/2005 | Orbay | |
| 2005/0165395 A1 | 7/2005 | Orbay et al. | |
| 2005/0165400 A1 | 7/2005 | Fernandez | |
| 2005/0171544 A1 | 8/2005 | Falkner | |
| 2005/0182405 A1 | 8/2005 | Orbay et al. | |
| 2005/0182406 A1 | 8/2005 | Orbay et al. | |
| 2005/0187551 A1 | 8/2005 | Orbay et al. | |
| 2005/0192578 A1 | 9/2005 | Horst | |
| 2005/0234458 A1 | 10/2005 | Huebner | |

FOREIGN PATENT DOCUMENTS

| | | |
|---|---|---|
| CH | 611 147 | 5/1979 |
| DE | 2515430 | 11/1975 |
| DE | 4201531 | 7/1993 |
| DE | 4343117 | 6/1995 |
| EP | 0 053 999 | 6/1982 |
| EP | 0 410 309 | 1/1991 |
| EP | 0415837 A2 | 3/1991 |
| EP | 0471418 A1 | 2/1992 |
| EP | 0362049 B1 | 5/1992 |
| EP | 773004 A1 * | 5/1997 |
| EP | 1 250 892 A2 | 9/2003 |
| EP | 1 250 892 A3 | 9/2003 |
| FR | 742.618 | 3/1933 |
| FR | 2 254 298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | WO96/29948 | 10/1996 |
| WO | WO 97/47251 | 12/1997 |
| WO | WO01/21083 A1 | 3/2001 |
| WO | WO01/62136 A3 | 8/2001 |
| WO | WO 03/105712 A2 | 12/2003 |

OTHER PUBLICATIONS

MIfx Dorsal IM Plate, brochure, DVO Extremity Solutions, Sep. 2005.
Biomechanical Evaluation of the Schuhli Nut, Kolodziej, et al., *Clinical Orthopaedics and Related Research*, vol. 347, pp. 79-85, Feb. 1998.
Internal Fixation in Osteoporotic Bone, An, Y.H., p. 83, 2002.
*Zespol Bone Screws*, in *Mikromed—Catalogue 2004* (Nov. 2004), available at http://www.mikromed.pl/katalog/Main/main_eng.htm and http://www.mikromed.pl/katalog/zespol_eng/wkrety.htm.
*Zespol Bone Plates*, in *Mikromed—Catalogue 2004* (Nov. 2004), available at http://www.mikromed.pl/katalog/Main/main_eng.htm and http://www.mikromed.pl/katalog/zespol_eng/plytki.htm.
SmartLock Locking Screw Technology, advertisement, *The Journal of Hand Surgery*, vol. 30A, No. 1, Jan 2005.
*Biological Plating: A New Concept to Foster Bone Healing*, Synthes (USA), 1991.
Treatment by Plates of Anteriorly Displaced Distal Radial Fractures, Ducloyer, *Fractures of the Distal Radius*, pp. 148-152, 1995.
Management of Comminuted Distal Radial Fractures, Jupiter et al., *Fractures of the Distal Radius*, pp. 167-183, 1995.
Open Reduction of Intra-Articular Fractures of the Distal Radius, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
Design and Biomechanics of a Plate for the Distal Radius, Gesensway et al., *Journal of Hand Surgery*, vol. 20, No. 6, pp. 1021-1027, 1995 (abstract only provided).
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
Prospective Multicenter Trial of a Plate for Dorsal Fixation of Distal Radius Fractures, Ring et al., *The Journal of Hand Surgery*, vol. 22A, No. 5, pp. 777-784, Sep. 1997.
Treatment of Displaced Intra-Articular Fractures of the Distal End of the Radius With Plates, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.
TriMed Wrist Fixation System brochure, TriMed, Inc., 1997.
SCS/D Distal Radius Plate System brochure, Avanta Orthopaedics, 1997.
Intra-Articular Fractures of the Distal Aspect of the Radius, Trumble et al., *Journal of Bone and Joint Surgery*, vol. 80A, No. 4, pp. 582-600, Apr. 1998.
Complications of the AO/ASIF Titanium Distal Radius Plate System (π Plate) in Internal Fixation of the Distal Radius: A Brief Report, Kambouroglou et al., *Journal of Hand Surgery*, vol. 23A, No. 4, pp. 737-741, Jul. 1998.
SCS/V Distal Radius Plate Volar brochure, Avanta Orthopaedics, 1998.
Delayed Rupture of the Flexor Pollicis Longus Tendon After Inappropriate Placement of the π Plate on the Volar Surface of the Distal Radius, Nunley et al., *Journal of Hand Surgery*, vol. 24, No. 6, pp. 1279-1280, Nov. 1999.
TiMAX Pe.R.I. Small Fragment Upper Extremity description pages, DePuy ACE Medical Company, 1999.
The Distal Radius Plate Instrument and Implant Set technique guide, Synthes (USA), 1999.
Outcome Following Nonoperative Treatment of Displaced Distal Radius Fractures in Low-Demand Patients Older Than 60 Years, Young, *Journal of Hand Surgery*, vol. 25A, No. 1, pp. 19-28, Jan. 2000.
Comparison of Three Different Plating Techniques for the Dorsum of the Distal Radius: A Biomechanical Study, Peine et al., *Journal of Hand Surgery*, vol. 25A, No. 1, pp. 29-33, Jan. 2000.
Distal Radial Metaphyseal Forces in an Extrinsic Grip Model: Implications for Postfracture Rehabilitation, Putnam et al., *Journal of Hand Surgery*, vol. 25A, No. 3, pp. 469-475, May 2000.
TriMed Wrist Fixation System internet description pages, TriMed, Inc., 2001.
Titanium Distal Radius Plates description page, Synthes (USA), 2001.
Locon-T Distal Radius Plating System case study and surgical method, Wright Medical Technology, Inc., 2001.
Open Reduction and Internal Fixation of Unstable Distal Radius Fractures: Results Using the Trimed Fixation System, Konrath et al., *Journal of Orthopaedic Trauma*, vol. 16, No. 8, pp. 578-585, 2002.
Locon-T Distal Radius Plating System brochure, Wright Medical Technology, Inc., 2002.
Distal Radius Fracture, Tornetta, *Journal of Orthopaedic Trauma*, vol. 16, No. 8, pp. 608-611, 2002.

Comparison of Different Distal Radius Dorsal and Volar Fracture Fixation Plates: A Biomechanical Study, Osada et al., *Journal of Hand Surgery*, vol. 28A, No. 1, pp. 94-104, Jan. 2003.
Tendon Function and Morphology Related to Material and Design of Plates For Distal Radius Fracture Fixation: Canine Forelimb Model, Turner et al., Orthopaedic Research Society, Feb. 2003.
Fractures of the Distal Aspect of the Radius: Changes in Treatment Over the Past Two Decades, Simic, *Journal of Bone and Joint Surgery*, vol. 85-A, No. 3, pp. 552-564, Mar. 2003.
Palmar Plate Fixation of AO Type C2 Fracture of Distal Radius Using a Locking Compression Plate—A Biomechanical Study in a Cadaveric Model, Leung et al., *Journal of Hand Surgery*, vol. 28B, No. 3, pp. 263-266, Jun. 2003.
Functional Outcome and Complications Following Two Types of Dorsal Plating for Unstable Fractures of the Distal Part of the Radius, Rozental et al., *Journal of Bone and Joint Surgery*, vol. 85, No. 10, pp. 1956-1960, 2003 (abstract only provided).
Fixation of Unstable Fractures of the Volar Rim of the Distal Radius with a Volar Buttress Pin®, Hooker et al., 2003.
Results of Palmar Plating of the Lunate Facet Combined with External Fixation for the Treatment of High-Energy Compression Fractures of the Distal Radius, Ruch et al., *J. Orthop. Trauma*, Vo. 18, No. 1, pp. 28-33, Jan. 2004.
Synthes Volar Distal Radius Locking Plate internet description page, Orthocopia, LLC, 2004.
VAL Plate description page, US Implants, undated.
Esser Complete Distal Radius Plate System, undated.
Proximal Humerus Fractures operative technique, Esser, undated.
McBride S.M.O. Stainless Steel Bone Plates brochure, DePuy, Inc., 1943.
Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.
Techmedica Bioengineers Keep Tabs on Your Needs brochure, Techmedica, Inc., 1991.
A Comparison of Unicortical and Bicortical End Screw Attachment of Fracture Fixation Plates, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
Treatment of Three- and Four-Part Fractures of the Proximal Humerus with a Modified Cloverleaf Plate, Esser, *Journal of Orthopaedic Trauma*, vol. 8, No. 1, pp. 15-22, 1994.
Ace Symmetry Titanium Upper Extremity Plates surgical technique brochure, Ace Medical Company, 1996.
The Ace Symmetry Titanium Upper Extremity Plates new product release brochure, Ace Medical Company, 1996.
Small Titanium Plates overview page, Synthes, p. 2a-33, Mar. 1997.
Congruent Distal Radius Plate System description, Acumed, Inc., Mar. 4, 1998.

Salvage of Tibial Pilon Fractures Using Fusion of the Ankle with a 90° Cannulated Blade Plate: A Preliminary Report, Morgan et al., *Foot & Ankle International*, vol. 20, No. 6, pp. 375-378, Jun. 1999.
*Scaphoid Protocols Using the Acutrak® Bone Screw System* brochure, Toby, published by Acumed, Inc., Dec. 7, 1999.
Single Unit Osteosynthesis brochure, Surfix Technologies, Sep. 2000.
Supracondylar Cable Plate brochure, Biomet Orthopedics, Inc., 2000.
Principle-Based Internal Fixation of Distal Humerus Fractures, Sanchez-Sotelo et al., *Techniques in Hand & Upper Extremity Surgery*, vol. 5, No. 4, pp. 179-187, Dec. 2001.
Congruent Plate System—The Mayo Clinic Congruent Elbow Plates brochure, Acumed, Inc., May 7, 2002.
Modular Hand System brochure, Acumed, Inc., Aug. 2002.
Modular Hand System brochure, Acumed, Inc., Sep. 2002.
Periarticular Plating System brochure, Zimmer, Inc., 2002.
Jplate Diaphysis Plates for Japanese brochure, Mizuho Co., Ltd., 2002.
An Axially Mobile Plate for Fracture Fixation, Abel et al., *Internal Fixation in Osteoporotic Bone*, pp. 279-283, 2002.
The Use of Interlocked 'Customised' Blade Plates in the Treatment of Metaphyseal Fractures in Patients with Poor Bone Stock, Palmer et al., *Injury, Int. J. Care Injured*, vol. 31, pp. 187-191, 2002.
3.5 mm LCP™ Proximal Humerus Plate technique guide, Synthes (USA), 2002.
Titanium Wire Plate Osteosynthesis System According to Dr. Gahr internet printout, Erothitan Titanimplantate AG, print date Feb. 6, 2003.
Bilder internet printout, Martin GmbH & Co. KG, print date Sep. 5, 2003.
International Search Report for PCT Patent Application Serial No. PCT/US03/22904, Dec. 4, 2003.
The Use of a Locking Custom Contoured Blade Plate for Peri-Articular Nonunions, Harvey et al., *Injury, Int. J. Care Injured*, vol. 34, pp. 111-116, 2003.
Salvage of Distal Tibia Metaphyseal Nonunions With the 90° Cannulated Blade Plate, Chin et al., *Clinical Orthopaedics and Related Research*, No. 409, pp. 241-249, 2003.
Rib Securing Clamped Plate internet printout, Sanatmetal, print date Sep. 22, 2004.
Acromio-Clavicular Plates description page, author and date unknown.
ECT Internal Fracture Fixation brochure, Zimmer, Inc., undated.
ECT Internal Fracture Fixation System order information brochure, Zimmer, Inc., undated.
NexGen Osteotomy System (OS) surgical technique brochure, Zimmer, Inc., undated.
Spider™ and Mini-Spider™ Limited Wrist Fusion System brochure, Kinetics Medical Incorporated, undated.
Spider™ Limited Wrist Fusion System brochure, Kinetics Medical Incorporated, undated.
Zuelzer Hook Plates description page, Codman & Shurtleff, Inc., p. 808, undated.

* cited by examiner

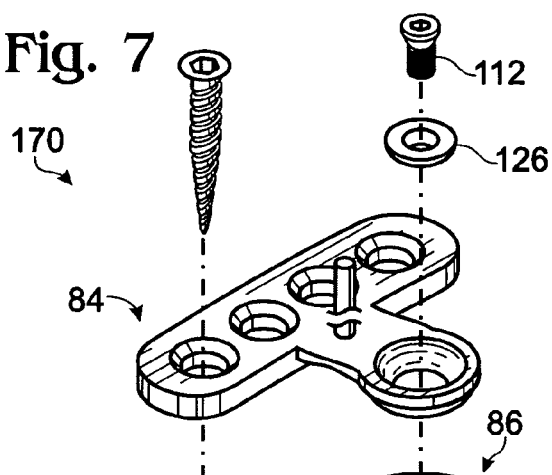
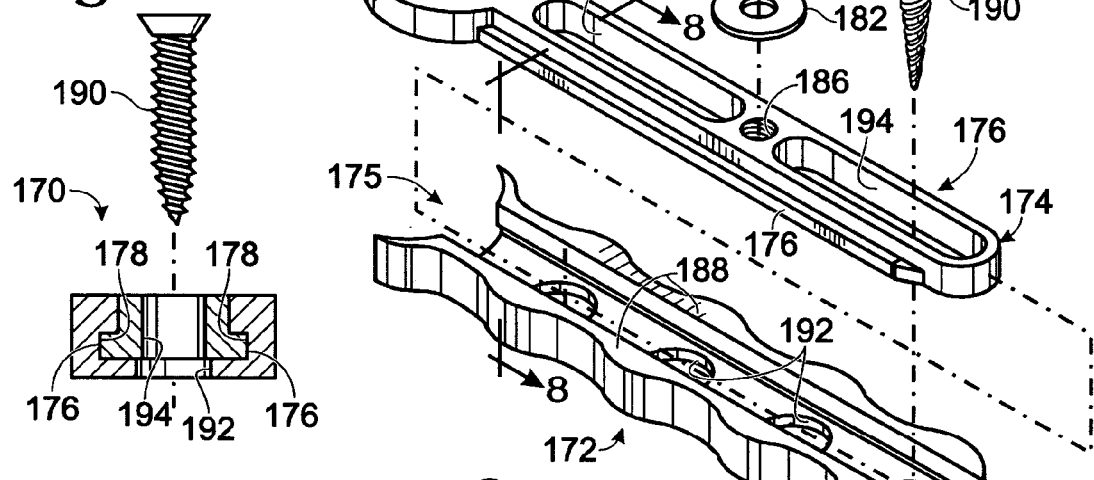
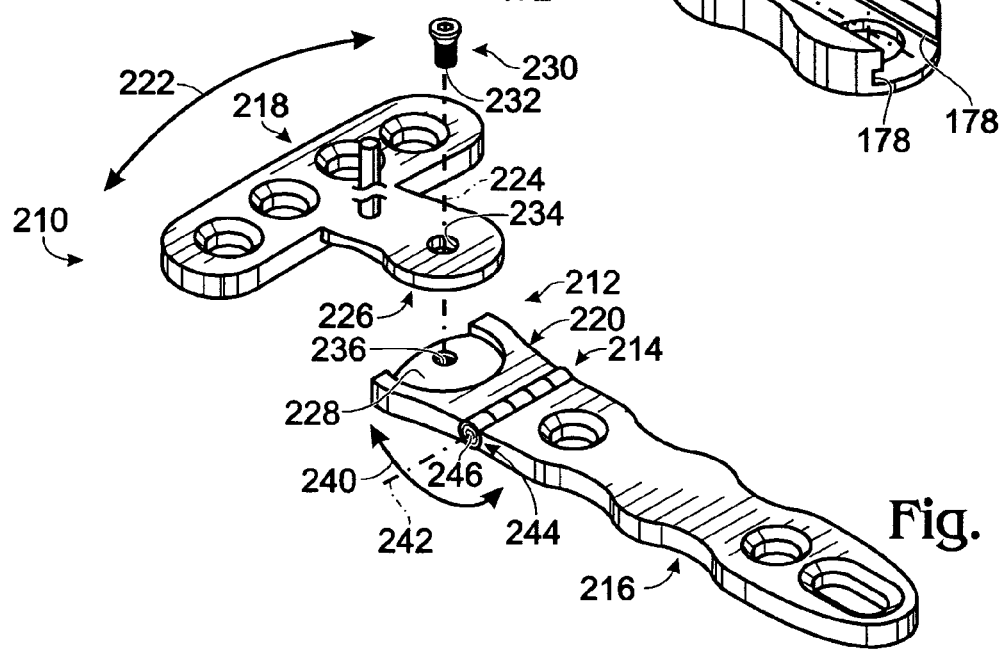

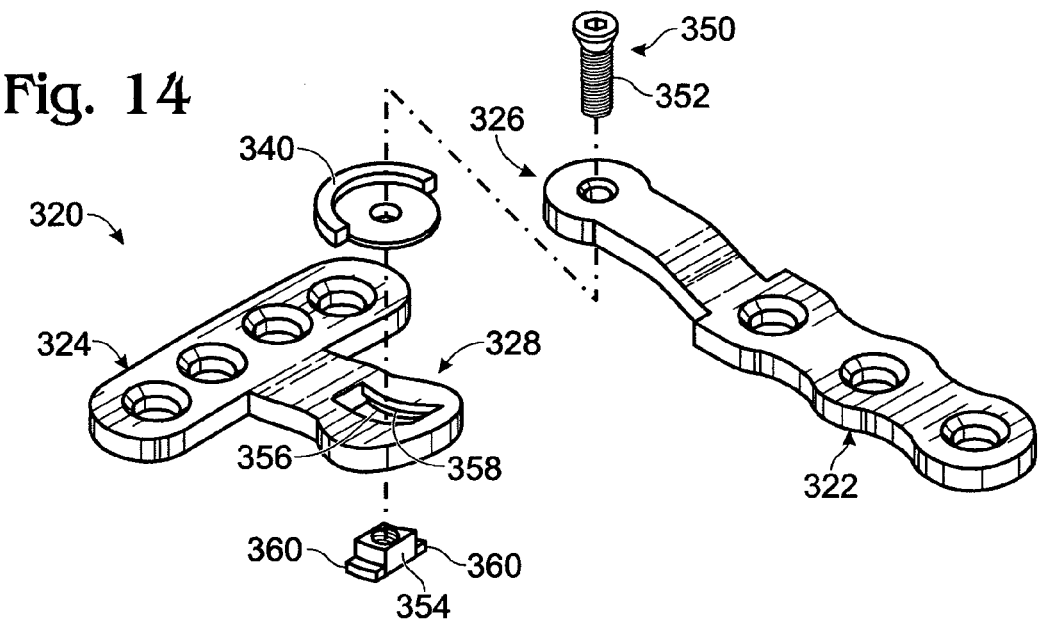
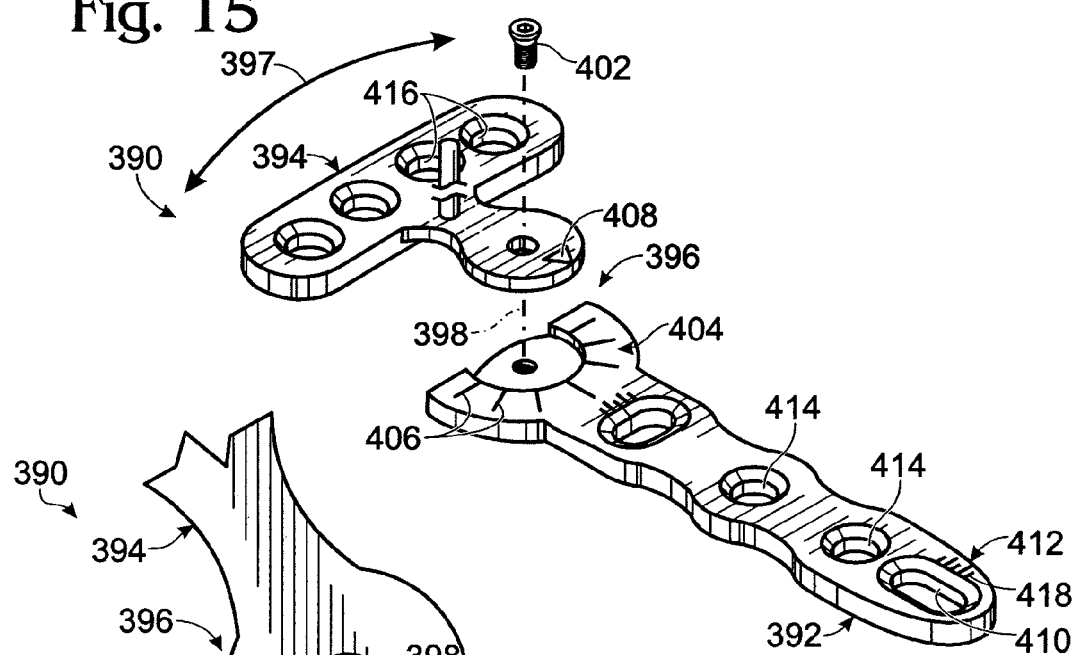
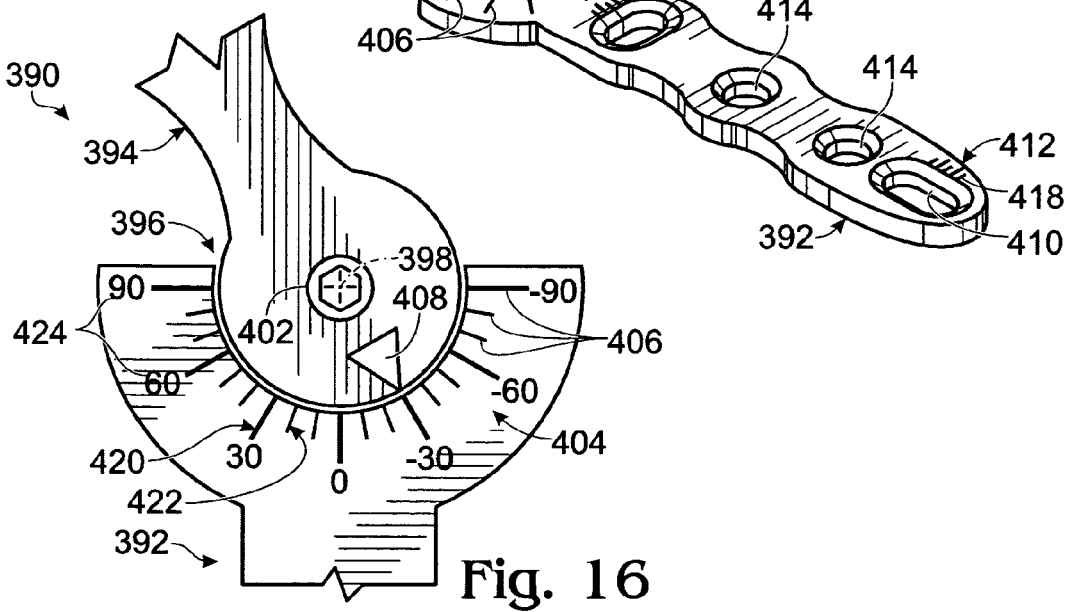

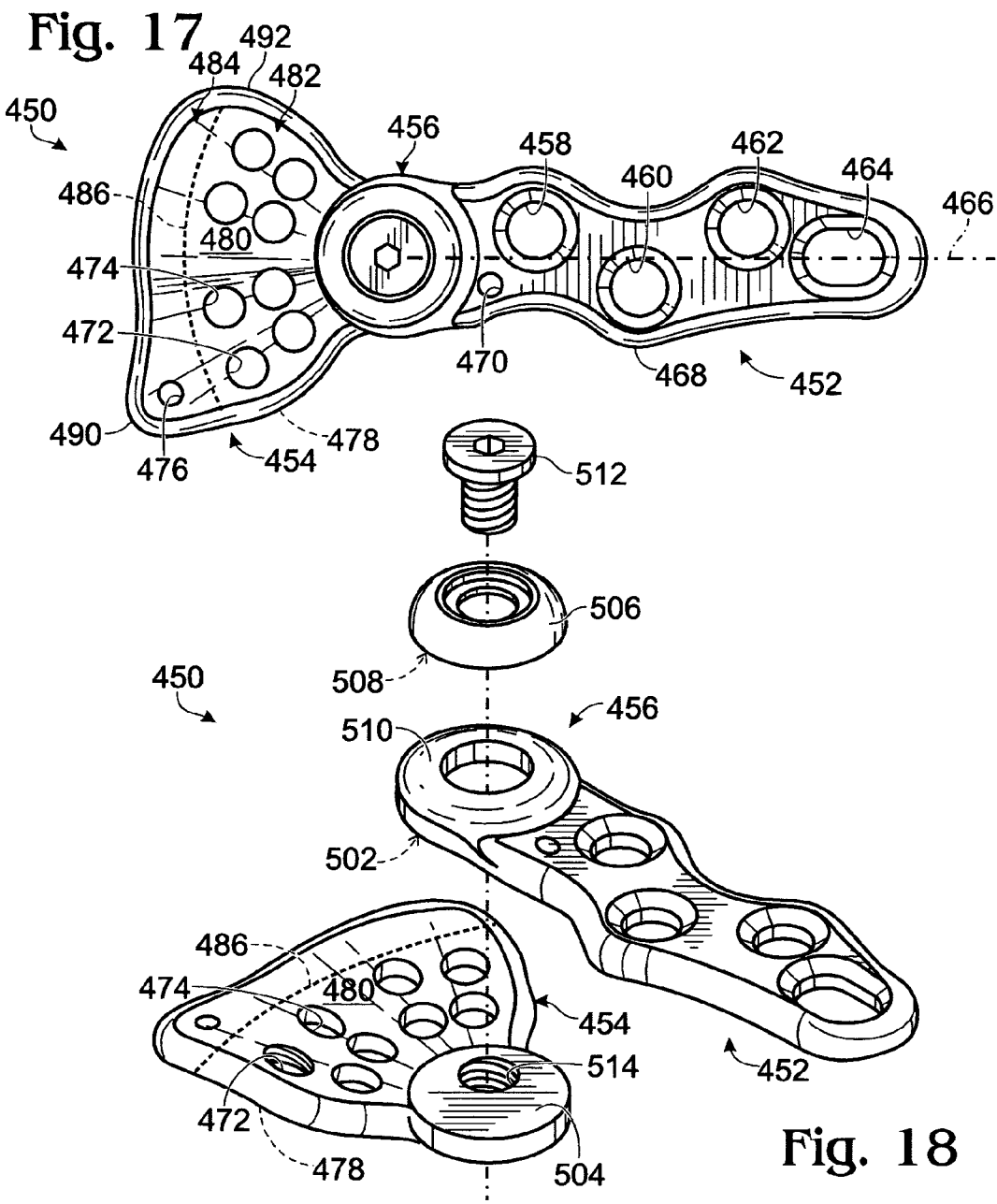
Fig. 17
Fig. 18
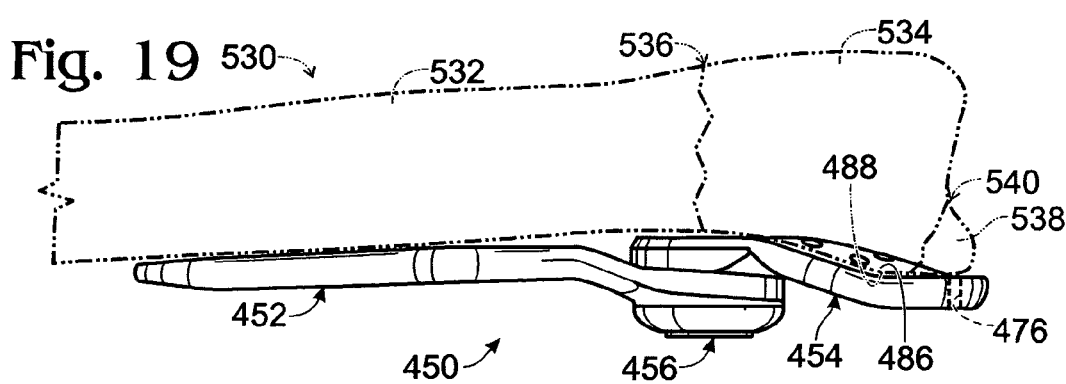
Fig. 19

BONE PLATES WITH REFERENCE MARKS

CROSS-REFERENCE TO PRIORITY APPLICATIONS

This application is based upon and claims the benefit under 35 U.S.C. § 119(e) of the following U.S. provisional patent applications: Ser. No. 60/427,908, filed Nov. 19, 2002; and Ser. No. 60/512,136, filed Oct. 17, 2003. Each of these provisional patent applications is incorporated herein by reference in its entirety for all purposes.

CROSS-REFERENCE TO OTHER APPLICATIONS

This application incorporates by reference in their entirety for all purposes the following U.S. patent applications: Ser. No. 10/716,719, filed Nov. 19, 2003, now U.S. Pat. No. 7,090,676; Ser. No. 10/717,401, filed Nov. 19, 2003, now U.S. Pat. No. 7,153,309; Ser. No. 10/717,402, filed Nov. 19, 2003; and Ser. No. 10/717,015, filed Nov. 19, 2003.

This application incorporates by reference in their entirety for all purposes the following U.S. provisional patent applications: Ser. No. 60/427,910, filed Nov. 19, 2002; Ser. No. 60/512,111, filed Oct. 17, 2003; Ser. No. 60/512,322, filed Oct. 17, 2003; and Ser. No. 60/512,323, filed Oct. 17, 2003.

This application incorporates by reference in its entirety for all purposes PCT Patent Application Serial No. PCT/US02/18623, filed Jun. 10, 2002.

FIELD OF THE INVENTION

The invention relates to bone plates. More specifically, the invention relates to bone plates having reference marks.

BACKGROUND

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become damaged should be repaired promptly and properly. Typically, a fractured or cut bone is treated using a fixation device, which reinforces the bone and keeps it aligned during healing. Fixation devices may include external fixation devices (such as casts and fixators) and/or internal fixation devices (such as bone plates, nails, and bone screws), among others.

Bone plates are sturdy internal devices, usually made of metal, that mount directly to the bone adjacent the fracture (or osteotomy). To use a bone plate to repair a discontinuity of a bone, a surgeon typically (1) selects an appropriate plate, (2) reduces the discontinuity (e.g., sets the fracture), and (3) fastens the plate to bone portions disposed on opposite sides of the discontinuity using suitable fasteners, such as screws and/or wires, so that the bone portions are fixed in position.

Despite direct access to the bone portions when applying a bone plate, the surgeon may have difficulty fixing the bone portions with the correct alignment. For example, one or more of the bone portions may be relatively small and/or displaced from the bone plate. As a specific example, in fixation of fractures of the distal radius, a distal bone portion(s) may be difficult to position properly. More generally, during attachment of any bone plate, fasteners may be misplaced or misdirected so that bone portions move away from a desired positioning as the fasteners are tightened. Accordingly, the relative position of bone portions may need to be adjusted after the bone plate has been secured to a bone to achieve proper reduction of a fracture.

SUMMARY

The invention provides bone plates having reference marks, and methods of using the bone plates to fix bones.

BRIEF DESCRIPTION OF THE DRAWINGS

FIG. 7 is an exploded view of a second example of a bone plate for fixing a fractured distal radius, in which axial and transverse portions of the bone plate can pivot and slide in relation to each other, in accordance with the present teachings.

FIG. 8 is a sectional view of the bone plate of FIG. 7 when assembled, viewed generally along line 8-8 of FIG. 7.

FIG. 9 is an exploded view of a third example of a bone plate for fixing a fractured distal radius, in which axial and transverse portions of the bone plate can pivot relative to one another about spaced orthogonal axes, in accordance with the present teachings.

FIG. 14 is an exploded view of the bone plate of FIG. 11.

FIG. 15 is an exploded view of a sixth example of a bone plate for fixing a fractured distal radius, with portions of the bone plate being pivotable and having reference marks to indicate the angular disposition of the plate portions, in accordance with the present teachings.

FIG. 16 is a fragmentary plan view of the bone plate of FIG. 15 in an assembled configuration, showing further aspects of the reference marks and illustrating use of the reference marks to measure the angular disposition of the plate portions.

FIG. 17 is a plan view of a seventh example of a bone plate for fixing a fractured distal radius, in which portions of the bone plate can pivot relative to each other about a plurality of axes, in accordance with the present teachings.

FIG. 18 is an exploded view of the bone plate of FIG. 17.

FIG. 19 is a side elevation view of the bone plate of FIG. 17 positioned on the volar surface of the distal radius for fixation of a distal radius fracture, in accordance with the present teachings.

DETAILED DESCRIPTION

The invention provides bone plates having reference marks, and methods of using the bone plates to fix bones.

The bone plates each may include a plurality of plate members connected by an adjustable (pivotable and/or translational) joint. The adjustable joint may be configured so that the shape and/or extent of the bone plate may be changed by adjusting the angular disposition of the plate members. The angular disposition may be adjusted by pivotal movement of a plate member about one axis or about a plurality of axes, and then the angular disposition may be fixed (locked). Each plate member may define one or more openings. The plate members may be configured to be secured to different regions of one bone or secured to different bones using fasteners placed in the openings.

The shapes and/or extent of the bone plates may be adjusted before, during, and/or after securing the bone plates to bone. When adjusted after attachment, movement of the plate members may change the relative disposition of attached bone portions, enabling a surgeon to improve the alignment and/or spacing of fractured or osteotomized bones, among others. As a result, reduction, fixation, and/or healing may be facilitated.

Bone plates having adjustable joints, as described herein, may be attached to or otherwise associated with bone using any suitable method or procedure. For example, a surgeon may (1) select an appropriate plate, (2) reduce (set) any fracture(s) or other discontinuities in the bone (at least partially), (3) fasten the plate to opposite sides of the fracture using suitable fasteners, such as screws and/or wires, (4) adjust the shape of the plate to adjust reduction of the fracture, and (5) fix the shape, so that attached portions of the bone are fixed in position. These steps may be performed manually and/or mechanically, for example, using a guide system as described in the following patent application, which is incorporated herein by reference: U.S. patent application Ser. No. 10/717,401, filed Nov. 19, 2003, now U.S. Pat. No. 7,153,309.

Figure 1:
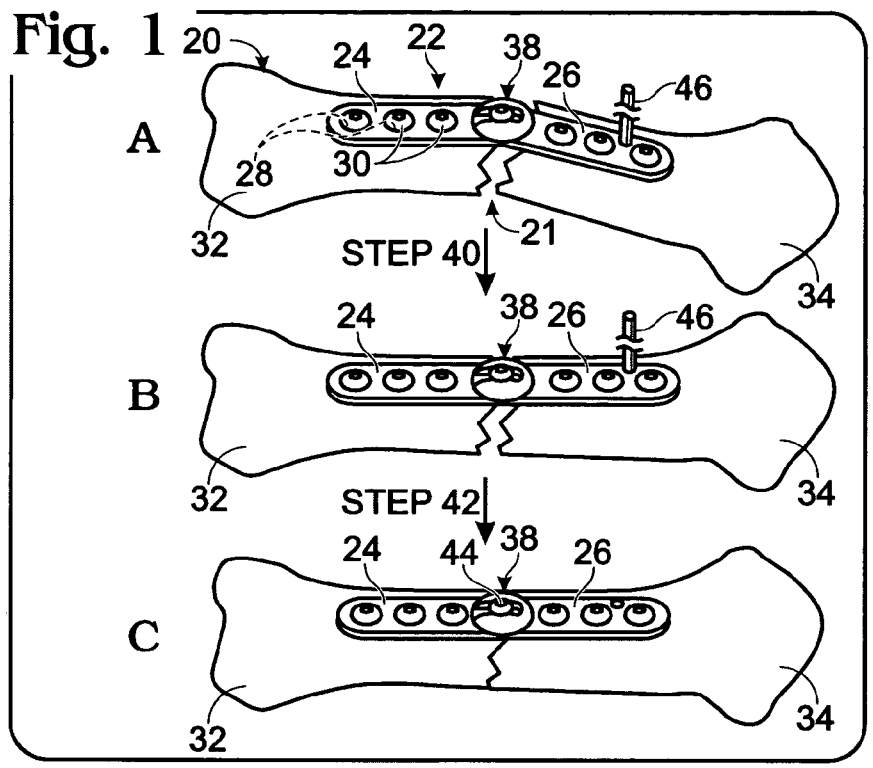
FIG. 1 is a series of views of a fractured bone showing its fracture being reduced and the bone being fixed with a pivotable bone plate, in accordance with the present teachings.

FIG. 1 shows a series of views of a fractured bone 20 with its fracture 21 being reduced and the bone being fixed with a pivotable bone plate 22.

FIG. 1A shows bone plate 22 secured to bone 20 without complete reduction of fracture 21. Bone plate 22 may include a first plate member 24 and a second plate member 26. Each of the plate members may define one or more openings 28 through which bone screws 30 (or other fasteners) may be placed into (or otherwise associated with) bone 20 to secure the plate members to the bone. The plate members may be secured to different portions or pieces 32, 34 of bone 20 disposed on opposing sides of the bone discontinuity, such as a fracture 21 or a cut within one bone (intra-bone fixation), or a joint between different bones (inter-bone fixation), among others. Plate members 24, 26 may be connected by a mechanical joint 38. Joint 38 may be configured to permit plate members 24, 26 to pivot and/or move translationally so that the angular disposition (the alignment) and/or spacing, respectively, of the plate members can be adjusted. In the present illustration, joint 38 permits both pivotal and translational movement of the plate members.

FIG. 1B shows an improved alignment of bone portions 32, 34 after pivotal movement, indicated as step 40, of first plate member 24 and second plate member 26 relative to one another. The pivotal movement may be about one axis, such as about an axis generally normal to the plate members, or about two or more axes. For example, joint 38 may be configured so that the first and second plate members can bend and twist relative to one another about three orthogonal axes.

FIG. 1C shows the result of optional translational movement, indicated as step 42, of first plate member 24 and second plate member 26 toward one another. The translational movement may adjust the spacing of the bone portions, for example, compressing (or distracting) the bone portions toward (or away from) one another, or shifting a plate member laterally. After pivotal and/or translational movement of the plate members, further relative movement of the plate members at joint 38 may be restricted by adjustment of a detent mechanism 44, such as a screw, to place joint 38 in a fixed configuration.

Pivotal and/or translational movement of the plate members relative to one another may be effected via any suitable mechanism, including manipulation of the bones and/or body portions connected to the bones, and/or manipulation of the bone plates and/or handles or other devices associated with the bone plates. Such manipulation may be performed by hand and/or using a tool. For example, in FIG. 1, pivotal and/or translational movement may be directed by a handle (or handles) 46 connected to one or more of the plate members (see FIGS. 1A and 1B). The handle may be grasped by hand or with a tool to apply a directional force, such as a torque, to one of the plate members. To increase torque by increasing the lever arm, the handle(s) may be positioned relatively far from the joint(s), and/or be relatively long. The handle may be removed after plate adjustment has been completed, as shown in FIG. 1C. In some embodiments, removal of the handle may include disconnecting the handle, for example, by rotation of the handle to disengage threads of the handle from a threaded opening of the bone plate.

Further aspects of the invention are described in the following sections, including (I) overview of bone plates, (II) plate members, (III) joints of bone plates, (IV) reference marks, and (V) examples.

I. Overview of Bone Plates

Bone plates as described herein generally comprise any relatively low-profile (or plate-like) fixation device configured to stabilize at least one bone by attachment to the bone. The fixation device may be configured to span a bone discontinuity (such as a fracture, a cut, a bone joint, etc.) so that the fixation device fixes the relative positions of bone portions disposed on opposing sides of the bone discontinuity. The fixation device generally is configured to be disposed in contact with an outer surface of the bone and thus may be positioned at least substantially exterior to the bone. The bone plate may be left in place permanently or removed after the associated bone has partially or completely healed.

The bone plates may be of a sturdy yet malleable construction. Generally, the bone plates should be stiffer and stronger than the section of bone spanned by the plates, yet flexible (e.g., springy) enough not to strain the bone significantly. Suitable Materials may be biocompatible materials (such as titanium or titanium alloys, cobalt chromium, stainless steel, plastic, ceramic, etc.) and/or bioabsorbable materials (such as polygalactic acid (PGA), polylactic acid (PLA), copolymers thereof, etc.), among others.

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue and rounded, burr-free surfaces to reduce the effects of such protrusion.

The bone plates may have at least one, and generally two or more, distinct anchor (or bone-attachment) portions, configured to be secured to a bone. Each anchor portion may be structured for a specific portion of a bone, generally to fit against a surface region of bone adjacent a bone discontinuity. For example, the bone plates may include a proximal anchor portion for attachment to a more proximal region of a bone, and a distal anchor portion for attachment to a more distal region of the same bone. In some embodiments, the bone plates may include a support (or buttress) portion connected to an anchor portion. The support portion may lack connective features that permit a direct connection of the support portion to the bone with one or more fasteners. Such a support portion may limit movement of a bone fragment using contact between the support portion and the fragment, and may include projections or prongs to engage the fragment more effectively.

The bone plates described herein may be sized and shaped to conform to particular portions of a bone (or bones). The plates may be generally elongate, with a length L, a width W, and a thickness T. Here, length L≧width W≧thickness T. In use, the long axis of the bone plates may be aligned with the long axis of the corresponding bone or may extend obliquely or even transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone or may have a nonlinear shape, such as for use near an end of a bone. In some embodiments, the plates may be generally T-shaped, including an axial portion, for attachment to a shaft portion of a bone, and a transverse portion connected to the axial portion, to provide a wider platform for attachment near an end of the bone. In some embodiments, the bone plates may be configured for use on both sides of the body, such as when the bone plates are bilaterally symmetrical. In some embodiments, the bone plates may be asymmetrical and configured for use on either the left or the right side of the body.

The bone plates described herein may be configured for use on any suitable bone of the human body and/or of another vertebrate species. Exemplary bones may include bones of the arms (radius, ulna, humerus), legs (femur, tibia, fibula, patella), hands, feet, the vertebrae, scapulas, pelvic bones, cranial bones, and/or the ribs and clavicles, among others. Particular examples where pivotable bone plates may be suitable include the distal radius (such as the volar surface of the distal radius) and the distal tibia.

The bone plates may include inner (bone-facing) and outer (bone-opposing) surfaces. One or both of these surfaces may be contoured generally to follow a surface of a target bone (or bones) for which the bone plates are intended, so that the bone plates maintain a low profile and fit onto the bone(s). For example, the inner surface of a plate may be generally complementary in contour to the bone surface. The outer surface may correspond in contour to the bone surface and may be complementary to the inner surface of the plate.

The thickness of the bone plates is defined by the distance between the inner and outer surfaces of the plates. The thickness of the plates may vary between plates and/or within the plates, according to the intended use. For example, thinner plates may be configured for use on a smaller bone and/or on a bone or bone region where soft tissue irritation is a greater concern. Thickness may be varied within the plates. For example, the plates may become thinner as they extend over protrusions (such as processes, condyles, tuberosities, and/or the like), reducing their profile and/or rigidity, among others. The thickness of the plates also may be varied to facilitate use, for example, to make the plates thinner where they typically need to be deformed by bending and/or twisting the plates. In this way, the plates may be thicker and thus stronger in regions where they typically do not need to be contoured, such as along the shaft of the bone.

The bone plates generally include a plurality of openings. The openings may be adapted to receive fasteners for securing the plates to bone. Alternatively, or in addition, the openings may be adapted to alter the local rigidity of the plates, to permit the plates to be manipulated with a tool (such as an attachable handle), and/or to facilitate blood flow to the fracture or surgical site to promote healing, among others.

The openings may have any suitable positions, sizes, and/or densities within each portion of a bone plate. The openings may be arrayed generally in a line along a portion of the plate, for example, centered across the width of the plate. Alternatively, the openings may be arranged nonlinearly, for example, disposed in a staggered arrangement. In some embodiments, the openings may be configured so that a set of bone screws can be directed along nonparallel paths, for example, to increase the purchase of the set of bone screws on bone. Further aspects of openings configured to direct bone screws along nonparallel paths are included the following patent application, which is incorporated herein by reference: U.S. Provisional Patent Application Ser. No. 60/512,111, filed Oct. 17, 2003.

The openings may have any suitable shape and structure. Exemplary shapes may include circular, elliptical, rectangular, elongate, etc. The openings may include counterbores configured, for example, to receive a head of a bone screw. The openings may be threaded or nonthreaded, and each bone plate may include one or more threaded and/or nonthreaded openings. In some embodiments, the plates may include one or a plurality of elongate openings (slots) extending axially and/or transversely along each bone plate. The slots may include counterbores that provide compression when bone screws are advanced against the counterbores. Alternatively, or in addition, the slots may be used to adjust the position of bone plates and/or plate portions relative to bone before the plates are fully secured to the bone. Further aspects of openings or slots that may be suitable for pivotable bone plates are described in more detail in the following patent applications, which are incorporated herein by reference in their entirety for all purposes: PCT Patent Application Serial No. PCT/US02/18623, filed Jun. 10 2002; and U.S. patent application Ser. No. 10/717,015, filed Nov. 19 2003.

The fasteners generally comprise any mechanism for affixing a bone plate to a bone, including screws, pins, and wires, among others. A preferred fastener is a bone screw, including unicortical, bicortical, and/or cancellous bone screws. Unicortical and bicortical bone screws typically have relatively small threads for use in hard bone, such as typically found in the shaft portion of a bone, whereas cancellous bone screws typically have relatively larger threads for use in soft bone, such as typically found near the ends (periarticular regions) of a long bone. Unicortical bone screws penetrate the bone cortex once, adjacent the bone plate. Bicortical bone screws penetrate the bone cortex twice, adjacent the bone plate and opposite the bone plate. Generally, unicortical screws provide less support than bicortical screws, because they penetrate less cortex. The size and shape of the fasteners may be selected based on the size, shape, and disposition of the openings, or vice versa. For example, unicortical bone screws may be suitable with particular arrangements of openings.

II. Plate Members

The anchor and/or buttress portions of a bone plate may be defined by separate components of the bone plate, termed plate members. Each plate member may define a different anchor and/or buttress portion of the bone plate. The pivotable bone plates described herein may include two or more plate members. In some embodiments, the bone plates may include at least three plate members, with each adjacent pair of plate members connected by a mechanical joint.

Plate members may have any suitable size and shape. Generally plate members may be sized and shaped according to a target bone portion for which each plate member is intended. Accordingly, the plate members of a bone plate may be configured to correspond to the anchor and/or buttress portions of a bone plate lacking a mechanical joint (that is, a unitary bone plate). In some embodiments, one or more of the plate members may be generally linear and/or generally T-shaped.

The plate members may be configured to be secured to (and/or engage) different portions of one bone or two or more bones. Accordingly, each plate member may include one or more connective features. A connective feature may be any structure of the plate member that permits coupling of the plate member to a fastener or to bone. Exemplary connective features may include a threaded opening to be engaged by a threaded fastener, a nonthreaded opening to be engaged by any screw and/or a wire, a hook, a pin, a prong, and/or the like. Each plate member may have no openings (for example, a plate member configured to buttress bone), one opening, or two or more openings. With two or more openings, the plate member may have all threaded openings, all nonthreaded openings, and/or a combination of threaded and nonthreaded openings, among others. In some embodiments, a plate member may have an opening configured to be engaged by a tool, such as a threaded or nonthreaded handle, to facilitate manipulation of the plate member, particularly after the plate member and/or its corresponding bone plate have been attached to bone.

III. Joints of Bone Plates

The bone plates described herein may include one or more joints. Each joint may be any connection between plate members that permits the plate members to move relative to one another. The joint(s) may be disposed to permit plate members of a bone plate to move rotationally (bend and/or twist) and/or translationally relative to one another, so that the angular disposition and/or spacing of the plate members may be adjusted. Each joint may have (1) an adjustable configuration in which the plate members can be moved independently, and (2) a fixed configuration in which the angular disposition and/or spacing of the plate members are fixed.

A joint may be formed at a bridge region between plate members. The bridge region may be defined by direct contact between plate members and/or may include one or more additional components, such as a bridge member, that spans a gap between the plate members. In some embodiments, the joint may include generally complementary surfaces of plate members that contact one another to guide sliding movement (translational and/or pivotal) of the surfaces (and thus the plate members) relative to one another. The generally complementary surfaces may have any suitable shape(s), including semi-spherical (or spherical), planar, curved (such as semi-cylindrical), etc.

The joint may be pivotable. A pivotable joint may be pivotable about a single axis or a plurality of two or more nonparallel (or parallel) axes. The axis may be the long axis of the plate (or of a plate member) to achieve twisting of the plate. Alternatively, or in addition, the axis may be a normal or "vertical" axis disposed generally orthogonal to a plane defined by the plate (or one of the plate members). Furthermore, the axis or axes may be one or more transverse or "horizontal" axes extending obliquely and/or orthogonally to the long axis of the plate or plate member. Pivotal movement about the normal and/or transverse axes provides bending of the plate.

Any suitable types of pivotable joints may be included in the bone plates. In some embodiments, the joint may permit pivotal movement about three orthogonal axes. An exemplary pivotable joint that allows plate members to be pivoted about three orthogonal axes is a ball joint (ball-in-socket). The ball joint includes at least one joint surface shaped generally as a complete sphere or as a portion of a sphere (semi-spherical). In some embodiments, a ball joint with a portion of a sphere may be preferred over a full sphere joint to minimize the profile of the joint. A ball joint may permit plate members to bend and twist relative to one another. Alternatively, the joint may be a hinge joint (a pin in a hole) that permits pivotal movement about only one axis. In some embodiments, the joint may be two or more joints that permit pivotal movement about spaced axes, such as spaced orthogonal axes (see Example 4 below). In some embodiments, the joint (or joints) may permit changes of angular disposition coupled with translational movement (see Example 5 below).

Any pivotable joint may be locked with a detent mechanism, to fix the angular disposition of the plate members. An exemplary detent mechanism includes a fastener, such as a screw or bolt. The fastener may be received threadedly to engage, compress, and/or expand a plate member(s) and/or an associated component, such as bridge member, to provide, for example, frictional engagement and thus restrict movement. In some embodiments, the detent mechanism may compress plate members together. In some embodiments, the detent mechanism may include a conical screw that expands a joint component, as the conical screw is advanced.

Any suitable structures may be included at the joint to guide and/or limit movement of plate members. Such guiding/limiting structures may include ridges and/or other projections that slide in grooves, a pin or fastener guided by a slot, and/or teeth/serrations received by a corresponding set of depressions or complementary teeth/serrations, among others. The guiding/limiting structures may allow continuous adjustment (for example, a ridge sliding in a groove or a ball rotating in a socket), or discrete adjustment positions (for example, serrations received by depressions). The guiding/limiting structures may restrict separation of the plate members (for example, a dovetail ridge received in a corresponding dovetail groove).

Sliding may be permitted by the guiding/limiting structures along one or plural axes. For example, sliding may be permitted along the long axis of the plate, to adjust the length of the plate. Alternatively, or in addition, sliding may be permitted transversely, for example, to offset plate members or to adjust the transverse position of a transversely extending plate member, such as in a T-shaped bone plate.

A slidable junction may be locked in position by any suitable detent mechanism. The detent mechanism may provide a continuous range of locked positions or only discrete locked positions. For example, the detent mechanism may be a fastener, such as a screw (or screws). The screw may be positionable within a slot defined by one plate member to allow a continuous range of adjustments. Alternatively, the screw may be received in one of a limited set of aligned apertures defined by the plate members to provide discrete locked positions. In other embodiments, the detent mechanism for translational (and/or pivotal) movement may be a tab or button that is bent, depressed, or otherwise moved into a retaining position.

Further aspects of adjustable bone plates having pivotable and/or sliding joints (and/or deformable portions) are described in the Examples below and in the following patent applications, each of which is incorporated herein by reference in its entirety for all purposes: U.S. patent application Ser. No. 10/716,719, filed Nov. 19, 2003, now U.S. Pat. No. 7,090,676; and U.S. patent application Ser. No. 10/717,402, filed Nov. 19, 2003.

IV. Reference Marks

The bone plates may include reference marks. The reference marks may be disposed adjacent a pivotable joint, a linearly slidable joint, and/or a slot, among others. The reference marks may indicate an angular disposition and/or a linear disposition of one portion of a bone plate relative to another. Alternatively, the reference marks may indicate a position of a bone screw within a slot. The reference marks may be any visible indicia on the bone plate. These indicia may be formed onto or into the plate during initial production, for example, by casting the plate using a mold configured to form the indicia (e.g., ridges or grooves in the mold to form grooves or ridges in the plate, respectively). Alternatively, or in addition, the indicia may be added to the plate after production, for example, by etching or cutting them into existing components of the plate, and/or adding them as additional components of the plate. In some cases, indicia may alternatively or additionally be included on a guide or template that is placed in apposition to the plate before or during installation, and then removed before the end of installation. Exemplary reference marks may include dots, dashes, symbols, numbers, letters, words, shapes, and/or colors, among others.

In some embodiments, a first plate member of a bone plate may have an arcuate (or linear) array of reference marks, and a second plate member of the bone plate may have a single reference mark or landmark. The arcuate array may include numbers or letters corresponding to different angular (or translational) positions. The numbers may include positive and negative numbers to indicate opposite directions of pivotal movement. The array of reference marks may be compared against the landmark during relative rotation (or translational movement) of one of the plate members relative to the other, to measure an angular (or translational) adjustment. Such an angular (or translational) adjustment may be predetermined, for example, by analysis of an x-ray, the bone itself, or tissue supported by the bone. Toward this end, corresponding or complementary reference marks may be included on instruments or tools used to select and/or install the bone plate, such as x-ray templates, measuring guides, and so on. Alternatively, or in addition, standard or typically used settings for the reference marks may be noted on the plate, for example, by identifying these marks using additional indicia (such as a star "★"). The adjustment may be assigned a numerical value, such as an angle or a distance. The reference marks may be configured to indicate a range of angle or distances, so that these marks indicate when the numerical value of adjustment has been reached during movement of the plate members. Pivotable bone plates with reference marks may be suitable for fixing osteotomies or fractures, or fixing different bones across bone joints, among others. Further aspects of pivotable bone plates with reference marks are described below in Example 7.

V. EXAMPLES

The following examples describe selected aspects and embodiments of the invention, including pivotable bone plates and exemplary uses of the pivotable bone plates to fix bones. These examples are included for illustration and are not intended to limit or define the entire scope of the invention.

Example 1

Exemplary Fracture for Fixation with Pivotable Bone Plates

Figure 2:
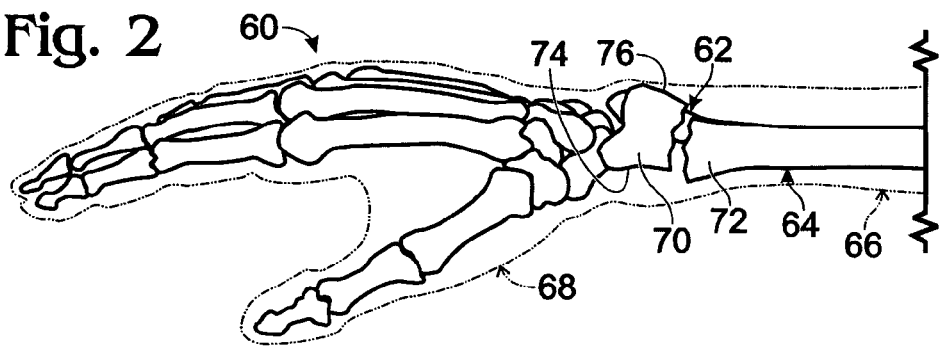
FIG. 2 is a lateral view of the bones of the right hand and distal forearm in which the radius has suffered a Colles' fracture, displacing and angulating a distal fragment of the radius dorsally.

This example describes an exemplary fracture that may be fixed with pivotable bone plates of the present teachings; see FIG. 2.

FIG. 2 shows an upper right extremity 60 exhibiting a Colles' fracture 62, which is a very common fracture of the distal radius 64 typically caused by using an outstretched hand to break a fall. The position of the fracture is indicated relative to the skin of the distal forearm 66 and hand 68, which is shown in phantom outline. In Colles' fracture 62, a smaller, distal bone fragment 70 may be displaced dorsally from a larger, proximal bone segment 72 of the radius bone. Colles' fracture 62 may be reduced and fixed with the pivotable bone plates described herein by placement of a bone plate on the volar (anterior or lower) side 74 of the radius. This placement may reduce or avoid tendon irritation that may occur with flexion when the bone plate is attached to the dorsal (posterior or upper) side 76 of the radius. Alternatively, the bone plates described herein may be used on the dorsal surface of the distal radius or on any other suitable bone(s) or bone surface(s).

Example 2

Bone Plate with Joint for Pivotal Movement about Three Axes

This example describes a bone plate, for use on a fractured distal radius, in which portions of the bone plate can bend and twist relative to each other; see FIGS. 3-6.

Figure 3:
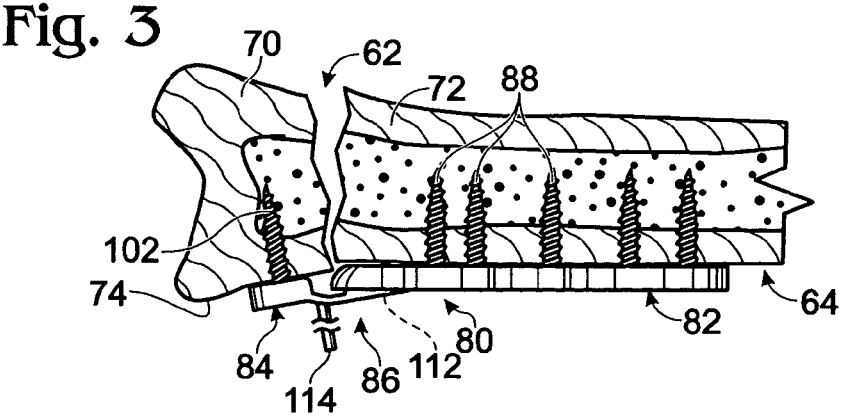
FIG. 3 is a sectional lateral-medial view of the fractured radius of FIG. 2, with a first example of a bone plate affixed to the volar surface of the fractured radius and configured for bending and twisting movement within the bone plate, in accordance with the present teachings.
Figure 4:
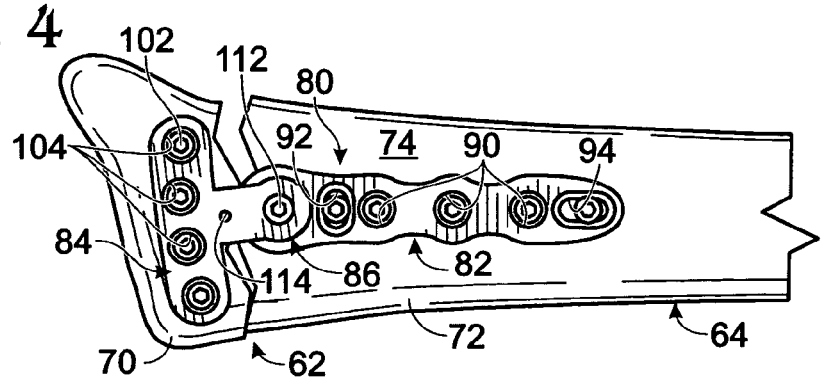
FIG. 4 is a volar view of the fractured radius and bone plate of FIG. 3.

FIGS. 3 and 4 show a lateral-medial sectional view and a volar view, respectively, of fractured radius 64 with a pivotable bone plate 80 affixed to radius adjacent volar surface 74. Pivotable bone plate 80 may include a proximal plate member 82 and a distal plate member 84 connected by a pivotable joint 86.

Proximal plate member 82 may have its long axis disposed generally parallel to the long axis of the radius. Plate member 82 may be generally linear. Plate member 82 may be secured to proximal segment 72 of the radius with a plurality of bone screws 88. Bone screws 88 may be bicortical bone screws or may be unicortical bone screws, as shown here. Bone screws 88 may be directed along parallel or nonparallel paths defined by openings 90-94 of the proximal plate member.

The paths the bone screws travel may be defined by a fit between fasteners (such as bone screws or pins) and the openings. The fit may be a close fit that at least substantially defines the angle at which a fastener travels through the bone plate and into bone, for placement of the fastener at a predefined angle. Alternatively, the fit may be a less restrictive fit that permits placement of the fastener at a selected angle within a range of angles. The type of fit for each fastener may be determined by a surgeon during installation of the bone plate by selection of each fastener.

A close fit may be defined by threaded or nonthreaded engagement of the fastener with the wall of the opening. The close fit may be defined by threaded engagement of a threaded fastener with a correspondingly threaded opening. The threaded engagement may predefine the angle and lock the axial position of the fastener relative to the screw's long axis. Alternatively, or in addition, the close fit may be defined by a close correspondence of the diameter of the fastener's shank and the diameter of the opening, particularly a cylindrical portion of the opening. The diameter of the fastener may be defined by a threaded or nonthreaded segment of the shank of the fastener (generally adjacent the head of the fastener). The diameter of the opening may be defined by a nonthreaded or threaded opening. Accordingly, a close fit at a predefined angle may be achieved by a nonthreaded or threaded shaft segment engaged by either of a threaded or nonthreaded opening.

A less restrictive fit may be defined by the size and/or shape of the opening in relation to the size and/or shape of the fastener. For example, the opening may have a diameter sufficiently greater than the diameter of the fastener to permit the fastener to achieve different angular dispositions within the opening. Alternatively, or in addition, the opening may have angled or curved walls to permit the fastener to pivot to different angular dispositions.

One or more of the openings, such as openings 92, 94, may be elongate openings or slots. The slots may be disposed axially and/or transversely on the plate member(s). The slots may have reference marks 98 disposed adjacent the slots (see FIG. 5). The reference marks may be configured to measure movement of the bone plate in the direction in which each slot extends. In some embodiments, the slots may be configured to permit axial and angular adjustment of the proximal plate member 82 with bone screws placed into bone from one or both of slots 92, 94, and before additional bone screws are placed through openings 90 and into bone. Further aspects of slots for positioning bone plates are included in the following patent application, which is incorporated herein by reference: U.S. patent application Ser. No. 10/717,015, filed Nov. 19, 2003.

Distal plate member 84 may have its long axis disposed transverse of the long axis of the radius. Plate member 84 may be generally T-shaped or fan-shaped. Plate member 84 may be secured to distal fragment 70 of the radius with a plurality of unicortical or bicortical bone screws 102 placed through openings 104 of the distal plate member and into bone. Openings 104 may be threaded, nonthreaded, or a mixture thereof. The bone screws may be selected for threaded or nonthreaded engagement with openings 104. Furthermore, each bone screw may be selected so that the angle of placement of a particular bone screw (or other fastener) is predefined by opening 104 or selectable within a range of angles, as described above for openings 90-94.

Figure 5:
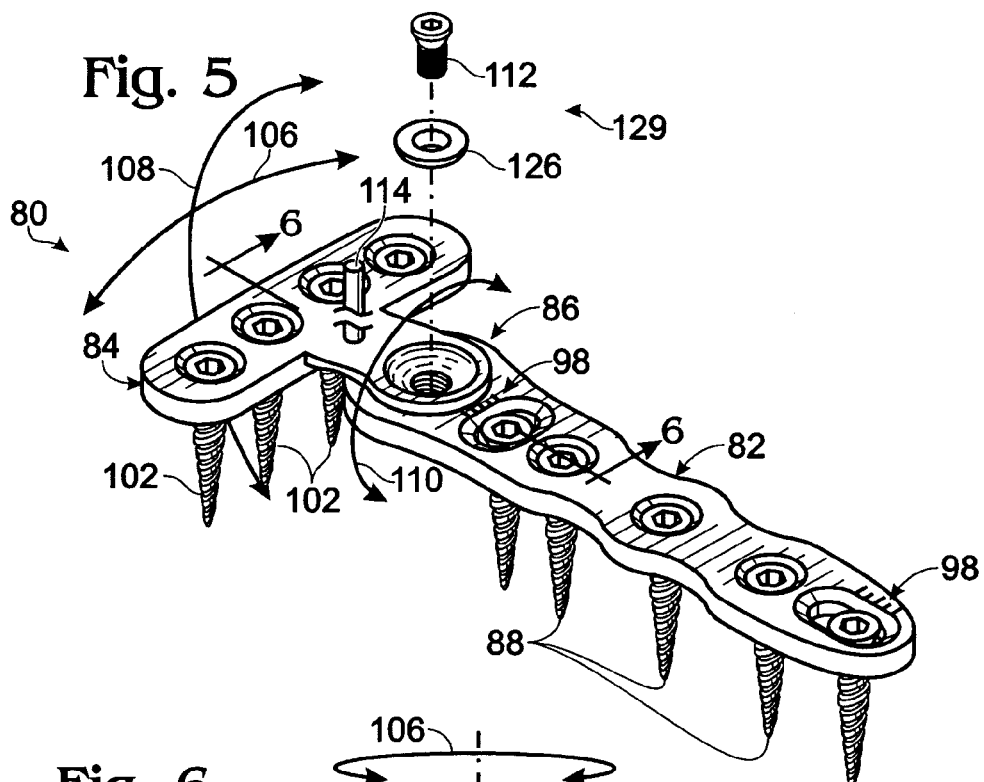
FIG. 5 is a partially exploded view of the bone plate of FIGS. 3 and 4 as seen from a position generally above the outer surface of the bone plate, in the absence of the distal radius and in the presence of bone screws.

Pivotable joint 86 may be configured to permit bending and twisting of distal plate member 84 relative to proximal plate member 82, before, during, and/or after the plate members are secured to the distal radius. FIG. 5 indicates bending movements 106, 108 about two axes and twisting movement 110 for the distal plate member.

FIGS. 3 and 4 show the position of bone plate 80 before final pivotal adjustment of the plate members and thus before final reduction of fracture 62. Pivotal adjustment may be accomplished, for example, by (1) placing joint 86 in an adjustable configuration by loosening lock screw 112, (2) rotating distal plate member 84 about one or more axes (such as clockwise in both FIGS. 3 and 4), by corresponding movement of connected handle 114, and (3) placing joint 86 in a fixed configuration by tightening lock screw 112 to fix the relative positions of the plate members and their attached bone portions.

Figure 6:
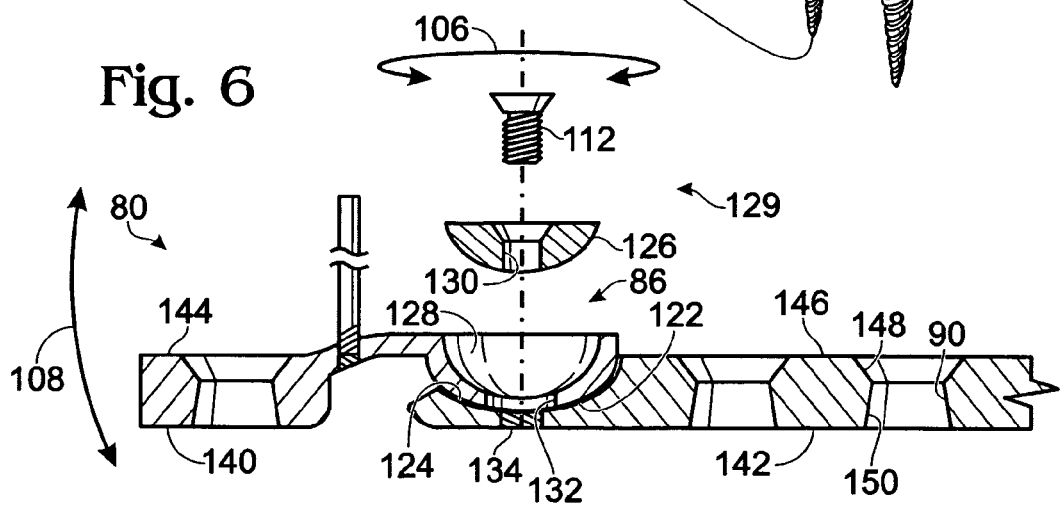
FIG. 6 is a fragmentary sectional view of the bone plate of FIG. 5, viewed generally along line 6-6 of FIG. 5.

FIGS. 5 and 6 shows additional aspects of pivotable bone plate, particularly aspects of pivotable joint 86. Joint 86 may include upper and lower semi-spherical surfaces 122, 124 included in the plate members. Semi-spherical surfaces 122, 124 may be convex and concave, respectively, and may have a similar radius of curvature. Accordingly, upper surface 122 may slide along lower surface 124 to achieve pivotal movement about three orthogonal axes. The upper and lower surfaces may be held in apposition by a semi-spherical retainer 126, generally in the form of a washer, and lock screw 112. The semi-spherical retainer may be configured to be received in a semi-spherical cavity 128 defined by the distal plate member. The retainer and semi-spherical cavity may have similar radiuses of curvature.

Pivotable joint 86 may include a detent mechanism 129 to restrict pivotal movement, In particular, the detent mechanism may include lock screw 112 received in openings 130, 132 of the retainer and distal plate member, respectively, and rotated into threaded engagement with a threaded bore 134 of the proximal plate member. The lock screw thus may be advanced or retracted to define the amount of frictional engagement between plate member surfaces 122, 124, to determine whether these surfaces are movable or fixed relative to one another. In some embodiments, the proximal plate member may include lower surface 124 and the distal plate member may include upper surface 126. Alternatively, or in addition, other aspects of the pivotable joint may be inverted from the configuration shown here, so that retainer 126 may be threaded and configured to serve as a nut disposed adjacent the bone. In this case, lock screw 112 may be placed through openings in each of the plate members from the outer surfaces of the plate members and into threaded engagement with the retainer.

Bone plate 80 may include inner surfaces 140, 142 and outer surfaces 144, 146 (see FIG. 6) on the plate members. Inner surfaces 140, 142 may be configured to be generally coplanar when the bone plate is in a neutral adjustment position, as shown here, or may not be coplanar. Openings, such as opening 90, may be defined between the inner and outer surfaces. The openings may include counterbores 148 and bores 150. Bores 150 may be cylindrical or may be flared toward the inner surface, among others.

Example 3

Bone Plate with Joints for Pivotal and Translational Movement

This example describes a bone plate, for use on a fractured distal radius, in which portions of the bone plate can bend, twist, and slide translationally relative to each other; see FIGS. 7 and 8.

Bone plate 170 may include a proximal plate member 172, a distal plate member 84, and a bridge member 174 connecting the two plate members. The bone plate may include two joints that permit pivotal and translational movement of the plate members, pivotable joint 86 and translational joint 175. Pivotable joint 86 may be configured as described above for Example 2 and will not be addressed further here.

Translational joint 175 may be defined by a telescoping relation of bridge member 174 with proximal plate member 172. In particular, bridge member 174 may include opposing, elongate ridges or guides 176 configured to be received in complementary elongate recesses or tracks 178 defined by the proximal plate member.

The axial position of bridge member 174 may be fixed by a detent mechanism 180. The detent mechanism may include a retainer 182 (such as a washer) and a fastener 184 (such as a screw or bolt). The fastener may be placed through the retainer and into threaded engagement with a threaded bore 186 of bridge member 174. Advancement of the fastener into the threaded bore may push retainer 182 into engagement with retention surfaces 188 of the proximal plate member 172, thereby restricting translation movement. The retainer may be loosened to permit further sliding at joint 175.

Before and/or after fixing joint 175, bone screws 190 may be placed through openings 192 of proximal plate member 172 and into bone. Bridge member 174 may include elongate passages 194 to permit the bone screws to be received over a continuous range of axial positions of the bridge member. The passages may be configured to permit the heads of bone screws to advance through the passages, or the heads of the bone screws may be engaged by the bridge member.

Example 4

Bone Plate with Spaced Pivotable Joints

This example describes a bone plate with a plurality of spaced joints configured for pivotal movement about orthogonal axes; see FIG. 9.

Bone plate 210 may include two pivotable joints 212, 214 connecting proximal plate member 216 and distal plate member 218 using bridge member 220. Pivotable joint 212 may permit pivotal movement, shown at 222 about a normal axis 224. Joint 212 may be defined by apposition of distal plate member 218 with bridge member 220 at contact surfaces 226, 228 of these members. Contact surfaces 226, 228 may be generally planar. The contact surfaces may include serrations or other complementary structures to restrict pivotal movement when a detent mechanism 230 is actuated.

Detent mechanism 230 may be provided by a connector 232, such as a screw, that passes through an opening 234 in distal plate member 218 and into threaded engagement with a threaded bore 236 of bridge member 220. Advancement of connector 232 may compress the distal plate member and the bridge member together to restrict pivotal movement. Surface features of contact surfaces 226, 228 may facilitate restricting movement when the detent mechanism is actuated.

Hinge joint 214 may permit pivotal movement, shown at 240, about a transverse axis 242. The hinge joint may be formed between bridge member 220 and proximal plate member 216. Detent mechanism 244 of the hinge joint may include a lock screw 246 that acts axially on the hinge joint, to compress the hinge joint parallel to axis 242. In some embodiments, the detent mechanism may act radially on the hinge joint, among others.

Example 5

Bone Plate with Integrated Joint for Sliding and Pivoting

Figure 10:
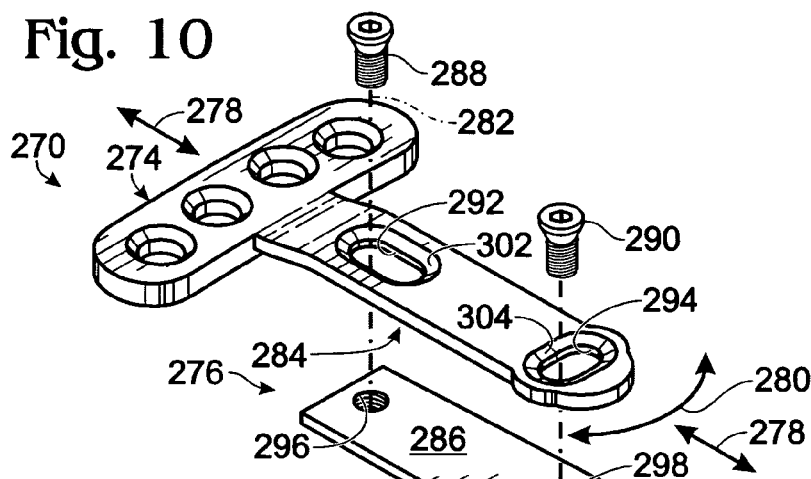
FIG. 10 is an exploded view of a fourth example of a bone plate for fixing a fractured distal radius, in which axial and transverse portions of the bone plate can pivot about one axis and slide translationally relative to one another, in accordance with the present teachings.

This example describes a bone plate, for fixing a fractured radius, in which the plate an integrated joint for sliding and pivoting; see FIG. 10.

Bone plate 270 may include a proximal plate member 272 and a distal plate member 274 connected at joint 276. Joint 276 may permit axial movement, shown at 278, and pivotal movement, shown at 280, about axis 282. The plate members may include contact surfaces 284, 286 that slide translationally and pivot relative to one another. The plate members may be connected by connectors 288, 290 (such as screws), that extend through elongate openings 292, 294 and into a threaded hole 296 and a threaded slot 29, respectively. The plate members may be adjusted positionally by pivotal and translational movement of the plate members, and then fixed in position by advancing connectors 288, 290 until their heads apply a compressive force to the counterbore surfaces 302, 304 of distal plate member 274.

Example 6

Bone Plate with Coupled Translational and Pivotal Movement

This example describes a bone plate, for fixing a fractured radius, in which the bone plate couples translational and pivotal movement; see FIGS. 11-14.

Figure 11:
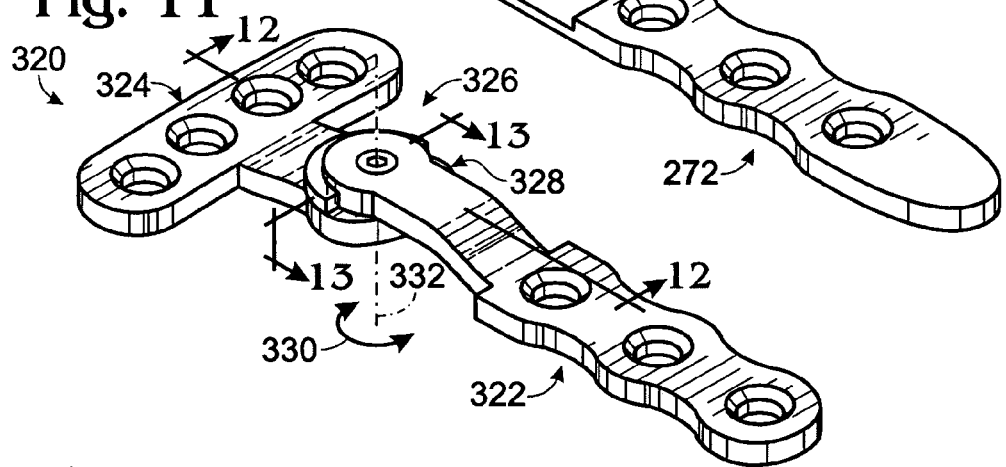
FIG. 11 is a view of a fifth example of a bone plate for fixing a fractured distal radius, in which axial and transverse portions of the bone plate can pivot about a normal axis and slide along a curved path, in accordance with the present teachings.

FIG. 11 shows a bone plate 320 having a proximal plate member 322 and a distal plate member 324 connected by two joints 326, 328. First joint 326 permits pivotal movement, shown at 330, about normal axis 332 and thus is similar to joint 212 of Example 4. Second joint 328 may be disposed under or over the first joint, among others, and may be configured to permit the plate members to slide translationally. However, the path along which the plate members slide may be arcuate, as described further below, so that the second joint permits coupled translational and circular movement.

Figure 12:
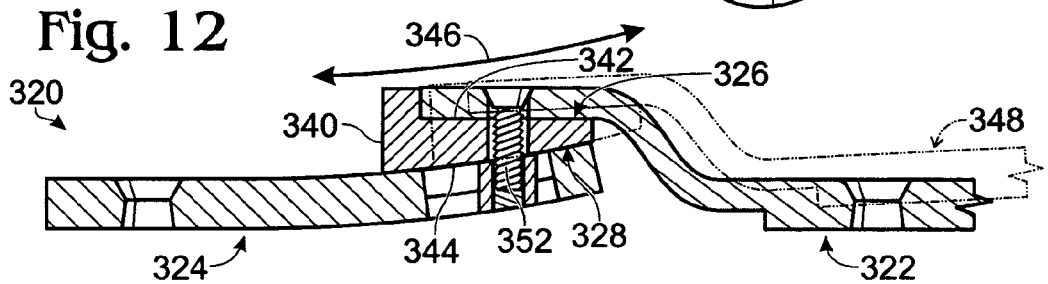
FIG. 12 is a fragmentary sectional view of the bone plate of FIG. 11, viewed generally along line 12-12 of FIG. 11.

FIG. 12 shows an axial sectional view of selected portions of bone plate 320. The plate members 322, 324 may be connected via a bridge member 340 that contacts the plate members on opposing surfaces 342, 344 of the bridge member. Upper surface 342 may provide a contact surface for pivotal movement of proximal plate member 322 at first joint 326. Lower surface 344 may provide a contact surface that defines a curved path, indicated at 346, along which distal plate member 324 slides. The curved path may be along a circular path, as indicated by an alternate position of proximal plate member 322 achieved by sliding along path 346, shown in phantom outline at 348.

Figure 13:
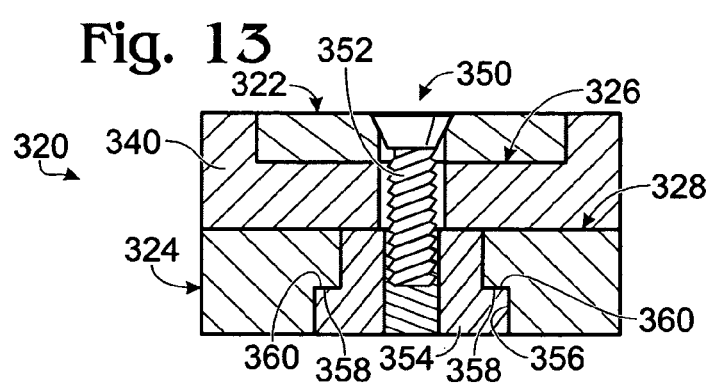
FIG. 13 is a sectional view of the bone plate of FIG. 11, viewed generally along line 13-13 of FIG. 11.

FIGS. 13 and 14 show a transverse sectional view and an exploded view, respectively, of bone plate 320. Joints 326, 328 may include a detent mechanism 350 having a connector 352. The connector may be a screw, among others, that extends through openings in proximal plate member 322 and bridge member 340. The screw may be received by a threaded nut 354 retained in a slot 356 defined by distal plate member 324. Slot 356 may be narrowed adjacent the bridge member to define walls 358 that engage shelves 360 of the nut, to retain the nut in slot 356.

Example 7

Bone Plate with Reference Marks

This example describes a bone plate with reference marks configured to measure angular and/or translational adjustment of the plate; see FIGS. 15 and 16.

FIG. 15 shows a bone plate 390 in an exploded view. Bone plate 390 may be configured, for example, to fix the position of cut bone portions after an osteotomy. Bone plate 390 may include an axial (or proximal) plate member 392 and a transverse (or distal) plate member 394 connected by a pivotable joint 396. Pivotable joint 396 may enable transverse plate member 394 to pivot, shown at 397, about one axis, such as normal axis 398. Alternatively, the pivotable joint may be configured to permit pivotal movement about two or more axes, as described elsewhere in the present teachings. Pivotable joint 396 may be adjustable and then fixable with a lock screw 402 or other detent mechanism.

Bone plate 390 may include an angular indicator mechanism 404 including angular reference marks 406 and a landmark 408. Angular reference marks 406 and landmark 408 may be disposed on different plate members 392, 394, respectively, or vice versa.

The bone plate also may include slot 410 and a linear indicator mechanism 412 that provides an axial measure of plate adjustment. Slot 410 may extend in alignment with the long axis of axial plate member 392. Slot 410 may receive a bone screw that guides linear sliding of the bone plate in relation to the bone screw (and thus underlying bone). Linear sliding may provide axial adjustment of the bone plate before the bone screw is fully tightened and/or before other bone screws are placed into bone from additional openings 414 of the bone plate. Linear sliding may be performed before and/or after bone screws have been placed into bone from openings 416 of the opposite (e.g., transverse) plate member(s). Positions within linear slot 410 may be indicated by reference marks 418 arrayed parallel to the slot adjacent an edge of the slot. Linear reference marks may have any suitable spacing and orientation, and may have any suitable form, including alphanumeric characters (such as numbers or letters), symbols, and/or other indicia that identify and/or distinguish individual marks.

FIG. 16 shows a plan view of angular indicator mechanism 404 of bone plate 390. Mechanism 404 may include angular reference marks 406 arrayed in an arcuate arrangement. The reference marks may include line segments that extend radially from pivot axis 398 and/or may include dots and/or dashes, among others. Adjacent pairs of reference marks 406 may define any suitable angle with pivot axis 398 of pivotable joint 396. For example, adjacent reference marks may define an angle of 1, 2, 5, or 10 degrees, among others. In some embodiments, reference marks 406 may include major and minor marks that are visibly distinguishable, such as longer marks, shown at 420, spaced here by thirty degrees, and flanking shorter marks, shown at 422, spaced here by ten degrees, among others. Indicator mechanism 404 also or alternatively may include alphanumeric characters, such as numbers 424, which identify particular references marks and/or serve as such marks. In some cases, standard (e.g., preferred and/or typically used) settings for the reference marks may be noted on the plate, for example, by using an alternative font, symbol, or size, and/or by identifying these marks using additional "standard setting" marks 426 (such as a star "★").

Landmark 408 may be configured to provide a site against which the reference marks 406 are compared, for example, to identify one of the reference marks that is most closely aligned with the landmark. For example, in the present illustration landmark 408 is aligned with the reference mark labeled as "−30" to indicate a 30 degree rotation of the transverse plate member from a neutral position of zero degrees. Angular reference mechanism 404 may be used to adjust the angular position of transverse plate member 392 by a predetermined angle. The angle may be predetermined by any suitable analysis, such as examining an x-ray of the bone to which the plate is attached, measuring the angle of bone or limb misalignment with an external measuring device, etc.

The uses for reference marks in bone plates with reference marks may extend to pre- and/or postoperative analysis. For example, before installing a bone plate, a surgeon could "dial in" or otherwise preset approximate settings for the bone plate. The preset value could be determined from preoperative analysis (e.g., using x-ray templates and/or other measurement tools having corresponding or complementary reference marks), comparison with a corresponding uninjured feature on an opposite side of a patient's body (e.g., using measurements of an uninjured left radius to determine suitable preset values for an injured right radius), comparison with statistical data collected from a variety of patients (e.g., in the form of a lookup table), and so on. Alternatively, or in addition, after installing a bone plate, a surgeon could record the final settings, for possible postoperative use. In some cases, reference marks may be readable in situ using x-rays, magnetic resonance, and/or similar techniques, to allow noninvasive monitoring of the continued proper placement and adjustment of the plate postoperatively. Suitable reference marks for such use include changes or alterations in the thickness, profile, and/or composition of the plate, among others.

Example 8

Pivotable Bone Plate

This example describes another pivotable bone plate, for use on a fractured distal radius, in which portions of the bone plate can bend and twist relative to each other; see FIGS. 17-19. Some aspects of this bone plate are shared with the bone plate described above in Example 2 and are described in more detail therein.

FIG. 17 shows a bone plate 450 configured for use on a volar surface of the distal radius. Bone plate 450 may be asymmetrical and configured for use on only one side of the body, on the left radius in the present illustration. Bone plate 450 may include a proximal anchor portion 452, a distal anchor portion 454, and a pivotable joint 456 connecting the proximal and distal anchor portions.

Proximal anchor portion 452 may be an axial portion configured to be generally aligned with the long axis of the radius. Proximal anchor portion 452 may define a plurality of openings, 458-464, for receiving fasteners, such as bone screws. Proximal opening 464 may be a slot disposed in general alignment with the long axis of proximal anchor portion 452. Each of the openings may be threaded or nonthreaded and may include or lack a counterbore. In some embodiments, one or more of the openings, such as opening 458, may be configured as a transverse slot. At least a subset of the openings may be disposed in a staggered arrangement, such as on opposing sides of a central axis 466 of the plate, to direct bone screws along staggered, nonparallel paths, as described in U.S. Provisional Patent Application Ser. No. 60/512,111, filed Oct. 17, 2003. Accordingly, openings of this subset may define different paths of travel for bone screws based on different orientations of the walls of the openings and/or threads thereof. The perimeter of proximal anchor portion 452 may generally follow the disposition of the openings, shown at 468, to create a wavy or wiggly appearance to the proximal anchor portion when viewed from a position normal to a plane defined by the plate. Proximal anchor portion 452 also may include one or more smaller openings 470, configured, for example, to receive a fastener of smaller diameter, such as a wire.

Distal anchor portion 454 may be configured to be secured to the widened distal region of the radius. Accordingly, distal anchor portion 454 may be wider than proximal anchor portion 452 and may flare distally, to produce a fan-like shape, so that the plate overall is generally T-shaped. Distal anchor portion 454 may define a plurality of openings 472, 474 arrayed in a direction generally transverse to central axis 466 of the proximal anchor portion 452, when the plate is adjusted to a neutral position as shown here. Openings 472, 474 may be arrayed in one or more linear or arcuate rows, among others.

The distal openings may be threaded, shown at 472, or nonthreaded, shown at 474, or a combination thereof, as in the present illustration (see FIG. 18 also). Each opening may be configured to receive a bone screw or other fastener (such as a pin) at a fixed angle or at a selected angle with a range of angles. The choice between a fixed or variable angle may be defined by how closely the screw or other fastener fits into the opening, and/or whether threaded engagement is used to fix the angle of the screw/fastener, as described above in more detail in Example 2.

Distal anchor portion 454 may include one or more additional openings 476 disposed distally of openings 472, 474. Distal opening 476 may be used, for example, to receive a fastener placed into the styloid process of the distal radius, particularly when the styloid process has been fractured or cut.

Distal anchor portion 454 may be contoured to fit on the volar surface of the distal radius. Accordingly, the distal anchor portion 454 may have an inner surface 478 that is transversely convex and an outer surface 480 that is transversely concave, particularly in a proximal section 482 of distal anchor portion 454. A distal section 484 of distal anchor portion 454 may be configured to be disposed distally of a volar-distal rim of the radius. Accordingly, distal anchor portion 454 may include a transverse contour 486, such as a slight depression, at the junction between proximal and distal sections 482, 484. Transverse contour 486 may be configured to receive the volar-distal rim 488 of the radius (see FIG. 19). The perimeter of distal anchor portion 454 may be shaped to correspond generally to the outline of the distal radius. For example, the distal-lateral perimeter 490 of the distal anchor portion 454 may be more angular and the distal-medial perimeter 492 more rounded.

FIG. 18 shows bone plate 450 and particularly pivotable joint 456 in an exploded view. The pivotable joint may include semi-spherical surfaces 502, 504 of the proximal and distal anchor portions 452, 454, respectively. These semi-spherical surfaces may be complementary so that they can slide on each other about three orthogonal axes. A retainer 506 may include a semi-spherical cavity 508 so that the retainer can be received by a second semi-spherical surface 510 of the proximal anchor portion 452. A fastener 512, such as a screw, may be placed through the retainer and proximal anchor portion 452 and into threaded engagement with a threaded bore 514 of distal anchor portion 454. The fastener may be turned in opposing directions to provide adjustable and fixed configurations of the bone plate. In some embodiments, joint 456 may permit pivotal movement about one or two axes and/or may permit translational movement, as described elsewhere the present teachings. The relative disposition of anchor portions 452, 454 may be adjusted with a tool that engages one or both of the portions, such as in one or more of the openings of the plate.

FIG. 19 shows bone plate 450 disposed on the volar surface of distal radius 530. Proximal anchor portion 452 may be secured to proximal bone region 532, and distal anchor portion 454 to distal bone region 534. Pivotable joint 456 may be disposed adjacent a distal facture 536 of the bone. Distal anchor portion 454 may extend over volar-distal rim 488 so that styloid process 538 may be secured to distal anchor portion 454 using a fastener placed in opening 476. Accordingly, a styloid discontinuity 540 (such as a fracture) may be spanned by distal anchor portion 454. The outer surface of the bone plate may be longitudinally concave and the inner surface longitudinally convex, as shown here, to follow the contour of the volar surface of the distal radius.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of bone fixation, comprising:
    securing a bone plate to at least one bone, or portion thereof, such that the bone plate is disposed under skin; and
    adjusting a relative disposition of plate members of the bone plate by relative movement of the plate members via an adjustable joint that connects the plate members and observation of reference marks, the reference marks being disposed on the bone plate and being configured to indicate a plurality of predefined adjustments,
    wherein the step of adjusting includes a step of manipulating a handle portion that is connected removably to a plate member.

2. The method of claim 1, wherein the step of securing includes a step of attaching the plate members to the at least one bone with a plurality of fasteners, and wherein the step of adjusting is performed after the step of attaching.

3. The method of claim 1, wherein the step of securing a bone plate includes a step of securing the bone plate to a radius bone.

4. The method of claim 1, wherein the step of adjusting a relative disposition includes a step of pivoting a plate member relative to another plate member.

5. The method of claim 1, wherein the step of adjusting a relative disposition includes a step of moving a plate member translationally relative to another plate member.

6. The method of claim 1, wherein the step of adjusting a relative disposition includes a step of observing reference marks that include numbers.

7. The method of claim 1, wherein the reference marks include a landmark on a plate member and a set of regularly spaced marks on another plate member, and wherein the step of adjusting includes a step of comparing the regularly spaced marks to the landmark to measure the relative disposition.

8. The method of claim 7, wherein at least one of the regularly spaced marks corresponds to a standard setting and is further denoted relative to the remaining regularly spaced marks by alternative and/or additional indicia.

9. A method of bone fixation, comprising:
securing plate members of a bone plate to a radius bone such that the plate members are disposed under skin; and
adjusting a relative angular disposition of the plate members by relative angular movement of the plate members and observation of reference marks, the reference marks being disposed on at least one of the plate members and being configured to indicate a plurality of predefined adjustments.

10. The method of claim 9, further comprising a step of selecting an adjustment to the relative angular disposition, wherein the adjustment is applied during the step of adjusting, wherein the step of securing includes a step of attaching the plate members to the radius bone with a plurality of fasteners, and wherein the step of attaching is performed before the step of selecting.

11. The method of claim 10, wherein the step of selecting an adjustment includes a step of measuring an angular disposition of one or more fragments of the radius bone.

12. The method of claim 9, further comprising a step of cutting the radius bone before the step of securing to form a cut region flanked by fragments of a radius bone.

13. The method of claim 12, wherein the step of cutting excises a segment of the radius bone.

14. The method of claim 9, the predefined adjustments corresponding to a set of predefined numerical values, further comprising a step of selecting a numerical value before the step of adjusting, wherein the step of adjusting includes a step of moving at least one of the plate members until the reference marks indicate that the numerical value has been reached.

15. The method of claim 9, further comprising a step of presetting the relative disposition by relative movement of the plate members prior to the steps of securing plate members and adjusting a relative angular disposition.

16. The method of claim 9, wherein the step of securing includes a step of attaching the plate members to the radius bone with a plurality of fasteners, and wherein the step of adjusting is performed after the step of attaching.

17. The method of claim 9, wherein the step of adjusting a relative disposition includes a step of pivoting a plate member relative to another plate member.

18. The method of claim 9, wherein the step of adjusting the relative angular disposition further includes a step of moving a plate member translationally relative to another plate member.

19. The method of claim 9, wherein the step of adjusting a relative disposition includes a step of observing reference marks that include numbers.

20. The method of claim 9, wherein the reference marks include a landmark on a plate member and a set of regularly spaced marks on another plate member, and wherein the step of adjusting includes a step of comparing the regularly spaced marks to the landmark to measure the relative disposition.

21. The method of claim 20, wherein at least one of the regularly spaced marks corresponds to a standard setting and is further denoted relative to the remaining regularly spaced marks by alternative and/or additional indicia.

* * * * *